(12) United States Patent
Laughner et al.

(10) Patent No.: US 9,687,167 B2
(45) Date of Patent: Jun. 27, 2017

(54) MEDICAL DEVICES FOR MAPPING CARDIAC TISSUE

(71) Applicant: BOSTON SCIENTIFIC SCIMED, INC., Maple Grove, MN (US)

(72) Inventors: Jacob I. Laughner, St. Paul, MN (US); Shibaji Shome, Arden Hills, MN (US); Scott A. Meyer, Lakeville, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 47 days.

(21) Appl. No.: 14/633,672

(22) Filed: Feb. 27, 2015

(65) Prior Publication Data

US 2015/0257671 A1    Sep. 17, 2015

Related U.S. Application Data

(60) Provisional application No. 61/951,266, filed on Mar. 11, 2014.

(51) Int. Cl.
*A61B 5/04* (2006.01)
*A61B 5/0452* (2006.01)
(Continued)

(52) U.S. Cl.
CPC ............ *A61B 5/0452* (2013.01); *A61B 5/042* (2013.01); *A61B 5/046* (2013.01); *A61B 5/0422* (2013.01);
(Continued)

(58) Field of Classification Search
CPC ... A61B 5/0452; A61B 5/0422; A61B 5/7264; A61B 5/046; A61B 5/6852; A61B 5/042;
(Continued)

(56) References Cited

U.S. PATENT DOCUMENTS

| 4,433,380 A | 2/1984 | Abele et al. |
| 4,690,152 A | 9/1987 | Juncosa |

(Continued)

FOREIGN PATENT DOCUMENTS

| EP | 1190671 A2 | 3/2002 |
| EP | 2258263 B1 | 8/2012 |

(Continued)

OTHER PUBLICATIONS

International Preliminary Report on Patentability issued in PCT/US2014/063148, mailed May 12, 2016, 9 pages.

(Continued)

*Primary Examiner* — Rex R Holmes
(74) *Attorney, Agent, or Firm* — Faegre Baker Daniels LLP

(57) ABSTRACT

Medical devices and methods for making and using medical devices are disclosed. A method of mapping electrical activity of a heart may comprise sensing a plurality of signals with a plurality of electrodes positioned within the heart. The method may further comprise separating the plurality of signals into a first group of signals and a second group of signals, and generating a data set that includes at least one known data point and one or more unknown data points. In some examples, the at least one known data point is generated based on the first group of signals.

7 Claims, 14 Drawing Sheets

(51) Int. Cl.
  *A61B 5/042* (2006.01)
  *A61B 5/00* (2006.01)
  *A61B 5/046* (2006.01)
  *G06K 9/00* (2006.01)
  *A61B 18/14* (2006.01)
  *A61B 18/00* (2006.01)

(52) U.S. Cl.
  CPC .......... *A61B 5/6852* (2013.01); *A61B 5/7253* (2013.01); *A61B 5/7264* (2013.01); *G06K 9/00536* (2013.01); *A61B 18/1492* (2013.01); *A61B 2018/00214* (2013.01); *A61B 2018/00267* (2013.01); *A61B 2018/00357* (2013.01); *A61B 2018/00577* (2013.01); *A61B 2018/00839* (2013.01)

(58) Field of Classification Search
  CPC ........ A61B 5/7253; A61B 2018/00839; A61B 2018/00267; A61B 2018/00577; A61B 2018/00357; A61B 2018/00214; G06K 9/00536
  See application file for complete search history.

(56) References Cited

U.S. PATENT DOCUMENTS

| | | |
|---|---|---|
| 5,254,088 A | 10/1993 | Lundquist et al. |
| 5,383,874 A | 1/1995 | Jackson et al. |
| 5,485,849 A | 1/1996 | Panescu et al. |
| 5,487,391 A | 1/1996 | Panescu |
| 5,494,042 A | 2/1996 | Panescu et al. |
| 5,527,292 A | 6/1996 | Adams et al. |
| 5,546,940 A | 8/1996 | Panescu et al. |
| 5,577,509 A | 11/1996 | Panescu et al. |
| 5,582,609 A | 12/1996 | Swanson et al. |
| 5,595,183 A | 1/1997 | Swanson et al. |
| 5,598,848 A | 2/1997 | Swanson et al. |
| 5,601,088 A | 2/1997 | Swanson et al. |
| 5,605,157 A | 2/1997 | Panescu et al. |
| 5,609,157 A | 3/1997 | Panescu et al. |
| 5,630,425 A | 5/1997 | Panescu et al. |
| 5,647,870 A | 7/1997 | Kordis et al. |
| 5,657,755 A | 8/1997 | Desai |
| 5,687,737 A | 11/1997 | Branham et al. |
| 5,688,267 A | 11/1997 | Panescu et al. |
| 5,702,386 A | 12/1997 | Stern et al. |
| 5,711,305 A | 1/1998 | Swanson et al. |
| 5,722,402 A | 3/1998 | Swanson et al. |
| 5,722,403 A | 3/1998 | McGee et al. |
| 5,722,416 A | 3/1998 | Swanson et al. |
| 5,732,698 A | 3/1998 | Swanson et al. |
| 5,735,846 A | 4/1998 | Panescu et al. |
| 5,740,808 A | 4/1998 | Panescu et al. |
| 5,752,518 A | 5/1998 | McGee et al. |
| 5,755,715 A | 5/1998 | Stern et al. |
| 5,769,847 A | 6/1998 | Panescu et al. |
| 5,792,064 A | 8/1998 | Panescu et al. |
| 5,795,303 A | 8/1998 | Swanson et al. |
| 5,797,903 A | 8/1998 | Swanson et al. |
| 5,797,905 A | 8/1998 | Fleischman et al. |
| 5,810,802 A | 9/1998 | Panescu et al. |
| 5,830,213 A | 11/1998 | Panescu et al. |
| 5,833,621 A | 11/1998 | Panescu et al. |
| 5,836,874 A | 11/1998 | Swanson et al. |
| 5,840,076 A | 11/1998 | Swanson et al. |
| 5,846,238 A | 12/1998 | Jackson et al. |
| 5,846,239 A | 12/1998 | Swanson et al. |
| 5,848,969 A | 12/1998 | Panescu et al. |
| 5,853,409 A | 12/1998 | Swanson et al. |
| 5,853,411 A | 12/1998 | Whayne et al. |
| 5,868,680 A | 2/1999 | Steiner et al. |
| 5,868,736 A | 2/1999 | Swanson et al. |
| 5,871,483 A | 2/1999 | Jackson et al. |
| 5,876,336 A | 3/1999 | Swanson et al. |
| 5,879,348 A | 3/1999 | Owens et al. |
| 5,891,136 A | 4/1999 | McGee et al. |
| 5,904,651 A | 5/1999 | Swanson et al. |
| 5,904,680 A | 5/1999 | Kordis et al. |
| 5,906,614 A | 5/1999 | Stern et al. |
| 5,908,445 A | 6/1999 | Whayne et al. |
| 5,911,739 A | 6/1999 | Kordis et al. |
| 5,916,163 A | 6/1999 | Panescu et al. |
| 5,925,038 A | 7/1999 | Panescu et al. |
| 5,928,228 A | 7/1999 | Kordis et al. |
| 5,935,079 A | 8/1999 | Swanson et al. |
| 5,941,251 A | 8/1999 | Panescu et al. |
| 5,954,661 A | 9/1999 | Greenspon et al. |
| 5,954,662 A | 9/1999 | Swanson et al. |
| 5,961,513 A | 10/1999 | Swanson et al. |
| 5,968,040 A | 10/1999 | Swanson et al. |
| 6,014,581 A | 1/2000 | Whayne et al. |
| 6,014,590 A | 1/2000 | Whayne et al. |
| 6,022,346 A | 2/2000 | Panescu et al. |
| 6,030,379 A | 2/2000 | Panescu et al. |
| 6,030,382 A | 2/2000 | Fleischman et al. |
| 6,035,226 A | 3/2000 | Panescu |
| 6,047,218 A | 4/2000 | Whayne et al. |
| 6,049,732 A | 4/2000 | Panescu et al. |
| 6,053,912 A | 4/2000 | Panescu et al. |
| 6,056,745 A | 5/2000 | Panescu et al. |
| 6,070,094 A | 5/2000 | Swanson et al. |
| 6,071,278 A | 6/2000 | Panescu et al. |
| 6,076,012 A | 6/2000 | Swanson et al. |
| 6,086,532 A | 7/2000 | Panescu et al. |
| 6,095,150 A | 8/2000 | Panescu et al. |
| 6,101,409 A | 8/2000 | Swanson et al. |
| 6,101,410 A | 8/2000 | Panescu et al. |
| 6,106,460 A | 8/2000 | Panescu et al. |
| 6,106,522 A | 8/2000 | Fleischman et al. |
| 6,113,591 A | 9/2000 | Whayne et al. |
| 6,115,626 A | 9/2000 | Whayne et al. |
| 6,123,702 A | 9/2000 | Swanson et al. |
| 6,129,669 A | 10/2000 | Panescu et al. |
| 6,129,724 A | 10/2000 | Fleischman et al. |
| 6,162,184 A | 12/2000 | Swanson et al. |
| 6,165,169 A | 12/2000 | Panescu et al. |
| 6,171,306 B1 | 1/2001 | Swanson et al. |
| 6,179,835 B1 | 1/2001 | Panescu et al. |
| 6,183,468 B1 | 2/2001 | Swanson et al. |
| 6,188,924 B1 | 2/2001 | Swanson et al. |
| 6,192,266 B1 | 2/2001 | Dupree et al. |
| 6,197,021 B1 | 3/2001 | Panescu et al. |
| 6,206,831 B1 | 3/2001 | Suorsa et al. |
| 6,216,043 B1 | 4/2001 | Swanson et al. |
| 6,221,013 B1 | 4/2001 | Panescu et al. |
| 6,226,542 B1 | 5/2001 | Reisfeld |
| 6,233,491 B1 | 5/2001 | Kordis et al. |
| 6,245,061 B1 | 6/2001 | Panescu et al. |
| 6,245,065 B1 | 6/2001 | Panescu et al. |
| 6,256,540 B1 | 7/2001 | Panescu et al. |
| 6,289,239 B1 | 9/2001 | Panescu et al. |
| 6,293,943 B1 | 9/2001 | Panescu et al. |
| 6,301,496 B1 | 10/2001 | Reisfeld |
| 6,330,473 B1 | 12/2001 | Swanson et al. |
| 6,353,751 B1 | 3/2002 | Swanson et al. |
| 6,370,435 B2 | 4/2002 | Panescu et al. |
| 6,389,311 B1 | 5/2002 | Whayne et al. |
| 6,391,024 B1 | 5/2002 | Sun et al. |
| 6,428,536 B2 | 8/2002 | Panescu et al. |
| 6,456,864 B1 | 9/2002 | Swanson et al. |
| 6,456,867 B2 | 9/2002 | Reisfeld |
| 6,471,699 B1 | 10/2002 | Fleischman et al. |
| 6,487,441 B1 | 11/2002 | Swanson et al. |
| 6,488,679 B1 | 12/2002 | Swanson et al. |
| 6,490,468 B2 | 12/2002 | Panescu et al. |
| 6,494,880 B1 | 12/2002 | Swanson et al. |
| 6,500,172 B1 | 12/2002 | Panescu et al. |
| 6,508,765 B2 | 1/2003 | Suorsa et al. |
| 6,516,807 B1 | 2/2003 | Panescu et al. |
| 6,522,913 B2 | 2/2003 | Swanson et al. |
| 6,542,773 B2 | 4/2003 | Dupree et al. |
| 6,556,695 B1 | 4/2003 | Packer et al. |
| 6,565,511 B2 | 5/2003 | Panescu et al. |

(56) References Cited

U.S. PATENT DOCUMENTS

| | | |
|---|---|---|
| 6,569,160 B1 | 5/2003 | Goldin et al. |
| 6,597,955 B2 | 7/2003 | Panescu et al. |
| 6,615,073 B1 | 9/2003 | Panescu et al. |
| 6,625,482 B1 | 9/2003 | Panescu et al. |
| 6,647,281 B2 | 11/2003 | Morency |
| 6,652,513 B2 | 11/2003 | Panescu et al. |
| 6,658,279 B2 | 12/2003 | Swanson et al. |
| 6,668,198 B2 | 12/2003 | Swanson et al. |
| 6,735,465 B2 | 5/2004 | Panescu |
| 6,736,811 B2 | 5/2004 | Panescu et al. |
| 6,745,076 B2 | 6/2004 | Wohlgemuth et al. |
| 6,746,401 B2 | 6/2004 | Panescu |
| 6,788,969 B2 | 9/2004 | Dupree et al. |
| 6,790,206 B2 | 9/2004 | Panescu |
| 6,824,515 B2 | 11/2004 | Suorsa et al. |
| 6,895,267 B2 | 5/2005 | Panescu et al. |
| 7,194,294 B2 | 3/2007 | Panescu et al. |
| 7,364,546 B2 | 4/2008 | Panescu et al. |
| 7,505,810 B2 | 3/2009 | Harlev et al. |
| 7,515,954 B2 | 4/2009 | Harlev et al. |
| 7,565,208 B2 | 7/2009 | Harris et al. |
| 7,582,084 B2 | 9/2009 | Swanson et al. |
| 7,676,264 B1 | 3/2010 | Pillai et al. |
| 7,699,829 B2 | 4/2010 | Harris et al. |
| 7,729,752 B2 | 6/2010 | Harlev et al. |
| 7,774,051 B2 | 8/2010 | Voth |
| 7,794,404 B1 | 9/2010 | Gutfinger et al. |
| 7,869,854 B2 | 1/2011 | Shachar et al. |
| 7,925,349 B1 | 4/2011 | Wong et al. |
| 7,930,018 B2 | 4/2011 | Harlev et al. |
| 7,937,136 B2 | 5/2011 | Harlev et al. |
| 7,945,326 B1 | 5/2011 | Wong et al. |
| 7,946,995 B1 | 5/2011 | Koh et al. |
| 7,953,475 B2 | 5/2011 | Harlev et al. |
| 7,957,791 B2 | 6/2011 | Harlev et al. |
| 7,957,792 B2 | 6/2011 | Harlev et al. |
| 7,957,813 B1 | 6/2011 | Persson et al. |
| 8,010,196 B1 | 8/2011 | Wong et al. |
| 8,019,419 B1 | 9/2011 | Panescu et al. |
| 8,032,218 B2 | 10/2011 | Wong et al. |
| 8,038,625 B2 | 10/2011 | Afonso et al. |
| 8,065,005 B1 | 11/2011 | Wong et al. |
| 8,103,327 B2 | 1/2012 | Harlev et al. |
| 8,103,338 B2 | 1/2012 | Harlev et al. |
| 8,128,617 B2 | 3/2012 | Bencini et al. |
| 8,137,343 B2 | 3/2012 | Harlev et al. |
| 8,165,666 B1 | 4/2012 | Briggs et al. |
| 8,167,876 B2 | 5/2012 | Harlev et al. |
| 8,175,680 B2 | 5/2012 | Panescu |
| 8,202,224 B2 | 6/2012 | Gutfinger et al. |
| 8,208,999 B2 | 6/2012 | Wenzel et al. |
| 8,280,511 B2 | 10/2012 | Zhao et al. |
| 8,306,623 B2 | 11/2012 | Wong et al. |
| 8,364,253 B2 | 1/2013 | Voth |
| 8,369,922 B2 | 2/2013 | Paul et al. |
| 8,386,049 B2 | 2/2013 | Persson et al. |
| 8,406,866 B2 | 3/2013 | Deno et al. |
| 8,414,579 B2 | 4/2013 | Kim et al. |
| 8,449,535 B2 | 5/2013 | Deno et al. |
| 8,504,152 B2 | 8/2013 | Wenzel et al. |
| 8,504,153 B2 | 8/2013 | Wenzel et al. |
| 8,554,333 B2 | 10/2013 | Wu et al. |
| 8,571,647 B2 | 10/2013 | Harlev et al. |
| 8,600,497 B1 | 12/2013 | Yang et al. |
| 8,712,519 B1 | 4/2014 | Panescu et al. |
| 8,830,235 B1 | 9/2014 | Guskov et al. |
| 2001/0000791 A1 | 5/2001 | Suorsa et al. |
| 2001/0009976 A1 | 7/2001 | Panescu et al. |
| 2001/0018608 A1 | 8/2001 | Panescu et al. |
| 2001/0020126 A1 | 9/2001 | Swanson et al. |
| 2001/0025175 A1 | 9/2001 | Panescu et al. |
| 2001/0044585 A1 | 11/2001 | Dupree et al. |
| 2002/0058870 A1 | 5/2002 | Panescu et al. |
| 2002/0065465 A1 | 5/2002 | Panescu et al. |
| 2002/0099415 A1 | 7/2002 | Panescu et al. |
| 2002/0111548 A1 | 8/2002 | Swanson et al. |
| 2002/0115941 A1 | 8/2002 | Whayne et al. |
| 2002/0143250 A1 | 10/2002 | Panescu et al. |
| 2002/0161422 A1 | 10/2002 | Swanson et al. |
| 2002/0193790 A1 | 12/2002 | Fleischman et al. |
| 2002/0198520 A1 | 12/2002 | Coen et al. |
| 2003/0028118 A1 | 2/2003 | Dupree et al. |
| 2003/0055419 A1 | 3/2003 | Panescu et al. |
| 2003/0065322 A1 | 4/2003 | Panescu et al. |
| 2003/0078494 A1 | 4/2003 | Panescu et al. |
| 2003/0078509 A1 | 4/2003 | Panescu |
| 2003/0088244 A1 | 5/2003 | Swanson et al. |
| 2003/0093067 A1 | 5/2003 | Panescu |
| 2003/0093069 A1 | 5/2003 | Panescu et al. |
| 2003/0144655 A1 | 7/2003 | Panescu |
| 2003/0153907 A1 | 8/2003 | Suorsa et al. |
| 2003/0158477 A1 | 8/2003 | Panescu |
| 2003/0199863 A1 | 10/2003 | Swanson et al. |
| 2003/0208123 A1 | 11/2003 | Panescu |
| 2004/0015065 A1 | 1/2004 | Panescu et al. |
| 2004/0097803 A1 | 5/2004 | Panescu |
| 2004/0254437 A1 | 12/2004 | Hauck et al. |
| 2005/0177151 A1 | 8/2005 | Coen et al. |
| 2005/0197657 A1 | 9/2005 | Goth et al. |
| 2005/0215945 A1 | 9/2005 | Harris et al. |
| 2005/0245949 A1 | 11/2005 | Goth et al. |
| 2006/0030833 A1 | 2/2006 | Harris et al. |
| 2006/0064083 A1 | 3/2006 | Khalaj et al. |
| 2006/0089688 A1 | 4/2006 | Panescu |
| 2006/0135957 A1 | 6/2006 | Panescu |
| 2006/0184166 A1 | 8/2006 | Valle et al. |
| 2007/0055227 A1 | 3/2007 | Khalaj et al. |
| 2007/0073179 A1 | 3/2007 | Afonso et al. |
| 2007/0073286 A1 | 3/2007 | Panescu et al. |
| 2007/0156048 A1 | 7/2007 | Panescu et al. |
| 2007/0232949 A1 | 10/2007 | Saksena |
| 2007/0299351 A1 | 12/2007 | Harlev et al. |
| 2007/0299352 A1 | 12/2007 | Harlev et al. |
| 2007/0299353 A1 | 12/2007 | Harlev et al. |
| 2008/0190438 A1 | 8/2008 | Harlev et al. |
| 2008/0249424 A1 | 10/2008 | Harlev et al. |
| 2008/0262361 A1 | 10/2008 | Gutfinger et al. |
| 2009/0018597 A1 | 1/2009 | Wenzel et al. |
| 2009/0171274 A1 | 7/2009 | Harlev et al. |
| 2009/0171345 A1 | 7/2009 | Miller et al. |
| 2009/0177071 A1 | 7/2009 | Harlev et al. |
| 2009/0177072 A1 | 7/2009 | Harlev et al. |
| 2009/0253976 A1 | 10/2009 | Harlev et al. |
| 2009/0262109 A1 | 10/2009 | Markowitz et al. |
| 2009/0281439 A1 | 11/2009 | Harlev et al. |
| 2009/0287267 A1 | 11/2009 | Wenzel et al. |
| 2009/0299211 A1 | 12/2009 | Wenzel et al. |
| 2010/0004712 A1 | 1/2010 | Zhao et al. |
| 2010/0023085 A1 | 1/2010 | Wu et al. |
| 2010/0030294 A1 | 2/2010 | Wong et al. |
| 2010/0091834 A1 | 4/2010 | Cheung et al. |
| 2010/0094274 A1 | 4/2010 | Narayan et al. |
| 2010/0106009 A1 | 4/2010 | Harlev et al. |
| 2010/0106154 A1 | 4/2010 | Harlev et al. |
| 2010/0274150 A1 | 10/2010 | Harlev et al. |
| 2010/0286550 A1 | 11/2010 | Harlev et al. |
| 2010/0286551 A1 | 11/2010 | Harlev et al. |
| 2010/0305433 A1 | 12/2010 | Harlev et al. |
| 2010/0324414 A1 | 12/2010 | Harlev et al. |
| 2011/0028821 A1 | 2/2011 | Bojovic et al. |
| 2011/0105928 A1 | 5/2011 | Bojovic et al. |
| 2011/0112413 A1 | 5/2011 | Panescu et al. |
| 2011/0112414 A1 | 5/2011 | Panescu et al. |
| 2011/0112415 A1 | 5/2011 | Bojovic et al. |
| 2011/0125150 A1 | 5/2011 | Deno et al. |
| 2011/0160574 A1 | 6/2011 | Harlev et al. |
| 2011/0166472 A1 | 7/2011 | Björling et al. |
| 2011/0184300 A1 | 7/2011 | Shvilkin et al. |
| 2011/0190625 A1 | 8/2011 | Harlev et al. |
| 2011/0202113 A1 | 8/2011 | Persson et al. |
| 2011/0275949 A1 | 11/2011 | Harlev et al. |
| 2011/0282186 A1 | 11/2011 | Harlev et al. |
| 2011/0282187 A1 | 11/2011 | Harlev et al. |
| 2011/0306896 A1 | 12/2011 | Altmann |

(56) References Cited

U.S. PATENT DOCUMENTS

| | | | |
|---|---|---|---|
| 2012/0004533 | A1 | 1/2012 | Peng et al. |
| 2012/0053470 | A1 | 3/2012 | Wong et al. |
| 2012/0078077 | A1 | 3/2012 | Harlev et al. |
| 2012/0130267 | A1 | 5/2012 | Harlev et al. |
| 2012/0143030 | A1 | 6/2012 | Harlev et al. |
| 2012/0184858 | A1 | 7/2012 | Harlev et al. |
| 2012/0184863 | A1 | 7/2012 | Harlev et al. |
| 2012/0184864 | A1 | 7/2012 | Harlev et al. |
| 2012/0184865 | A1 | 7/2012 | Harlev et al. |
| 2012/0245481 | A1 | 9/2012 | Blanco et al. |
| 2012/0253161 | A1 | 10/2012 | Harlev et al. |
| 2012/0265054 | A1 | 10/2012 | Olson |
| 2012/0277574 | A1 | 11/2012 | Panescu |
| 2012/0283587 | A1 | 11/2012 | Gosh et al. |
| 2013/0035576 | A1 | 2/2013 | O'Grady et al. |
| 2013/0060245 | A1 | 3/2013 | Grunewald et al. |
| 2013/0096447 | A1 | 4/2013 | Dhawan et al. |
| 2013/0123775 | A1 | 5/2013 | Grunewald et al. |
| 2013/0137999 | A1 | 5/2013 | Wenzel et al. |
| 2013/0138003 | A1 | 5/2013 | Kaski |
| 2013/0173222 | A1 | 7/2013 | Voth |
| 2013/0204124 | A1 | 8/2013 | Duindam et al. |
| 2013/0226016 | A1 | 8/2013 | Narayan et al. |
| 2013/0274582 | A1 | 10/2013 | Afonso et al. |
| 2013/0303892 | A1 | 11/2013 | Zhao et al. |
| 2013/0303945 | A1 | 11/2013 | Blumenkranz et al. |
| 2014/0100440 | A1 | 4/2014 | Cheline et al. |
| 2014/0278321 | A1 | 9/2014 | Zhang et al. |
| 2014/0310016 | A1 | 10/2014 | Kenney et al. |
| 2015/0016749 | A1 | 1/2015 | Chen et al. |
| 2015/0065836 | A1* | 3/2015 | Thakur ............... A61B 5/0422 600/374 |
| 2015/0196214 | A1 | 7/2015 | Shuros et al. |
| 2015/0196215 | A1 | 7/2015 | Laughner et al. |
| 2015/0196216 | A1 | 7/2015 | Laughner et al. |
| 2015/0250399 | A1 | 9/2015 | Laughner et al. |

FOREIGN PATENT DOCUMENTS

| | | |
|---|---|---|
| WO | 2007035306 A2 | 3/2007 |
| WO | 2007137045 A2 | 11/2007 |
| WO | 2007146864 A3 | 12/2007 |
| WO | 2008097767 A2 | 8/2008 |
| WO | 2009085108 A1 | 7/2009 |
| WO | 2009123819 A2 | 10/2009 |
| WO | 2010051183 A1 | 5/2010 |
| WO | 2010058372 A1 | 5/2010 |
| WO | 2010123637 A2 | 10/2010 |
| WO | 2010129095 A2 | 11/2010 |
| WO | 2011021948 A1 | 2/2011 |
| WO | 2011142931 A1 | 11/2011 |
| WO | 2011142932 A1 | 11/2011 |
| WO | 2012092016 A1 | 7/2012 |
| WO | 2012097059 A1 | 7/2012 |
| WO | 2012097067 A1 | 7/2012 |
| WO | 2012151301 A1 | 11/2012 |
| WO | 2015066322 A1 | 5/2015 |
| WO | 2015106196 A1 | 7/2015 |
| WO | 2015106201 A1 | 7/2015 |
| WO | 2015106254 A1 | 7/2015 |
| WO | 2015134276 A1 | 9/2015 |

OTHER PUBLICATIONS

International Preliminary Report on Patentability issued in PCT/US2015/011013 mailed Jul. 28, 2016, 8 pages.

International Preliminary Report on Patentability issued in PCT/US2015/011025, mailed Jul. 28, 2016, 6 pages.

International Preliminary Report on Patentabiiity issued in PCT/US2015/011170 mailed Jul. 28, 2016, 7 pages.

Faes, L., et. al. Principal Component Analysis and Cluster Analysis for Measuring the Local Organization of Human Atrial Fibrillation. Med. Biol. Eng. Comput., 39(6): 656-663, 2001.

International Search Report and Written Opinion issued in PCT/US2015/018016, mailed May 20, 2015, 13 pages.

Mats, R. J., et. al. A Two-Stage Mechanism for Registration and Ciassification of ECG Using Gaussian Mixture Model. Pattern Recognition, 42(11): 2979-2988, 2009.

Blanchard, Susan M., et al., "Four Algorithms for Activation Detection from Unipolar Epicardial Electrograms", IEEE Transactions on Biomedical Engineering, 36(2):256-261, Feb. 1, 1989.

Blanchard, Susan M., et al., "Interpolating Unipolar Epicardial Potentials from Electrodes Separated by Increasing Distances", PACE and Clinical Electrophysiology, 12(12):1938-1955, Dec. 1, 1989.

Chen I-Ching, et al. "Radiofrequency Ablation Therapy in Concealed Left Free Wall Accessory Pathway With Decremental Conduction," The Cardiopulmonary and Critical Care Journal. CHEST. New York City, New York. pp. 107(1 ):40-45, Jan. 1995.

Corinna B. Brunckorst, et al. "Identification of the Ventricular Tachycardia Isthmus After lnfarction by Pace Mapping," Circulation Journal of the American Heart Assoication. Volume Circulation, American Heart Association. Dallas, Texas, 110:652-659, Aug. 2, 2004.

Deepak Bhakta, et al. "Principles of Electroanatornic Mapping," Indian Pacing and Electrophysiology Journal. Krannert Institute of Cardiology. Indianapolis, Indiana, 8(1 ):32-50, 2008.

Etienne M. Aliot, et al. "EHRA/HRS Expert Consensus on Catheter Ablation of Ventricular Arrhythmias," European Society of Cardiology. The European Heart Rhythm Association, 11:771-817, 2009.

Feifan Ouyang, et al. "Electroanatornic Substrate of Idiopathic Left Ventricular Tachycardia: Unidirectional Block and Macroreentry Wthin the Purkinje Network," Circulation Journal of the American Heart Association. American Heart Associatio. Dallas, Texas, 105(10):462-469, 2002.

He, Ye H., "An interactive graphical system for automated mapping and display of cardiac rhythms", Journal of Electrocardiology, vol. 32, No. 3, Jul. 1, 1999, pp. 225-241.

Hong Cao, et al. "FEM Analysis of Predicting Electrode-Myocardium Contact From RF Cardiac Catheter Ablation System Impedance," IEEE Transactions on Biomedical Engineering. IEEE Engineering in Medicine and Biology Society. Madison, Wisconsin. 49(6):520-526, Jun. 2002.

International Search Report and Written Opinion issued in PCT/US2014/063148, mailed Feb. 4, 2015, 11 pages.

International Search Report and Written Opinion issued in PCT/US2015/011013, mailed Sep. 4, 2015, 11 pages.

International Search Report and Written Opinion issued in PCT/US2015/011025, mailed Apr. 2, 2015, 8 pages.

International Search Report and Written Opinion issued in PCT/US2015/011170, mailed Apr. 28, 2015, 9 pages.

International Search Report and Written Opinion issued in PCT/US2015/017775, mailed May 26, 2015, 11 pages.

Jang-Zern Tsai, et al. "Dependence of Apparent Resistance of Four-Electrode Probes on Insertion Depth," IEEE Transactions on Biomedical Engineering. IEEE Engineering in Medicine and Biology Society. Madison, Wisconsin, 47(1):41-48, Jan. 2000.

Jang-Zern Tsai, et al. "Error Analysis of Tissue Resistivity Measurement. IEEE Transactions on Biomedical Engineering," IEEE Engineering in Medicine and Biology Society. Madison, Wisconsin, 49(5):484-494, May 2002.

Jason Ng, et al. "Undertanding and Interpreting Dominant Fequeny Analysis of AF Electrograms," J Cardiovasc Electrophysiol. Blackwell. Chicago, Illinois. 18(6):680-685, 2007.

Ji-Qiang Hu, et al. "The Characteristics of Verapamil-sensitive Idiopathic left Ventricular Tachycardia combined with a left accessory pathway and the effect of radiofrequency catheter ablation," Clinical Research Electrophysiology and Ablation. The European Society of Cardiology, Beijing, China. pp. 704-708, Jun. 30, 2011.

Joseph B. Morton, et al. "Sensitivity and Specificity of Concealed Entrainment for the Identification of Critical Isthmus in the Atrium: Relationship to Rate, Anatomic Location and Antidromic Penetration," Journal of the American College of Cardiology, Elsevier Science Inc. Melbourne, Australia. 39(5):896-906. Mar. 6, 2002.

Ken Okumura, et al. "Pathophysiology and Natural History Ventricular Tachycardia. Demonstration of the Presence of Slow Con-

(56) References Cited

OTHER PUBLICATIONS duction During Sustained Ventricular Tachycardia in Man: Use of Transient Entrainment of the Tachycardia," Department of Medicine, Case Western Reserve University/University Hospitals of Cleveland, Ohio and the University of Alabama at Birmingham; 75(2):369-378, Feb. 1987.

Koonlawee Nademanee, et al. "How to perform Electrogram-guided Atrial Fibrillation Ablation," The Pacific Rim Electrophysiology Research Institute. Heart Rhythm Society. Inglewood, California, 3(8):981-984, Aug. 2006.

Koonlawee Nademanee, et al. A New Approach for Catheter Ablation of Atrial Fibrillation: Mapping of the Electrophysiologic Substrate. Journal of the American College of Cardiology. Jun. 2, 2004. 43(11):2044-2053. Elsevier Inc. Inglewood, California; and Bangkok, Thailand.

Minglong Chen, et al. "Non-contact mapping and linear ablation of the left posterior fascicle during sinus rhythm in the treatment of idiopathic left ventricular tachycardia," European Society of Cardiology. vol. 7: pp. 138-144, Elsevier Ltd. China, 2005.

Nademanee K, et al. "Catheter Ablation of Atrial Fibrillation guided by complex Fractionated Atrial Electrogram Mapping of Atrial Fibrillation Substrate," Pacific Rim Eltrophysiology Research Institute. Elsevier Ltd. Los Angeles, California. 55(3):1-12, May 2010.

Prashanthan Sanders, et al. Spectral Analysis Identifies Sites of High-Frequency Activity Maintaining Atrial Fibrillation in Humans. Circulation Journal of the American Heart Association. The American Heart Association, Inc. Dallas, Texas, 112:789-797, Aug. 9, 2005.

Quan Ni, et al. "A Novel Interpolation Method of Electric Potential Fields in the Heart during Excitation," Annals of Biomedical Engineering. Biomedical Engineering Society. Salt Lake City, Utah. vol. 26:597-607, 1998.

Shiro Nakahara, et al. "Characterization of the Arrhythmogenic Substrate in Ischemic and Nonischemic Cardiomyopathy. Implications for Catheter Ablation of Hemodynamically Unstable Ventricular Tachycardia," Journal of the American College of Cardiology. Los Angeles, California, 55(21):2355-2365, May 25, 2010.

Stevenson WG, et al. "Identifying sites for Catheter Ablation of Ventricular Tachycardia," PubMed NCB I. MeSH Terms, Abstract, Jun. 1992.

Takeshi Tsuchiya. et al. "Significance of Late Diastolic Potential Preceding Purkinje Potential in Verapamil-Sensitive Idiopathic Left Ventricular Tachycardia." American Heart Association. Japan, pp. 2408-2413, May 11, 1999.

William G. Stevenson, et al. "Identification of Reentry Circuit Sites During Catheter Mapping and Radiofrequency Ablation of Ventricular Tachycardia Late After Myocardial Infarction," Circulation. American Heart Association. Los Angeles, California. 88(4)1 646-1670, Oct. 1993.

William G. Stevenson, et al. "Recording Techniques of Clinical Electrophysiology," J Cardiovasc Electrophysiol. Blackwell. Boston, Massachusetts. 16(9):1017-1022, 2005.

William G. Stevenson, et al. Journal of the American College of Cardiology. Fractionated Endocardial Electrograms are Associated With Slow Conduction in Humans: Evidence From Pace-Mapping, Los Angeles, California, 13(2):369-376, Feb. 1989.

Yilmaz, B., et. al. Usage of Spline Interpolation in Catheter-Based Cardiac Mapping. Turk. J. Elec. Eng. & Comp. Sci., 18(6):989-1002, 2010.

International Preliminary Report on Patentability issued in PCT/US2015/017775 mailed Sep. 22, 2016, 7 pages.

International Preliminary Report on Patentability issued in PCT/US2015/018016, mailed Sep. 22, 2016, 9 pages.

* cited by examiner

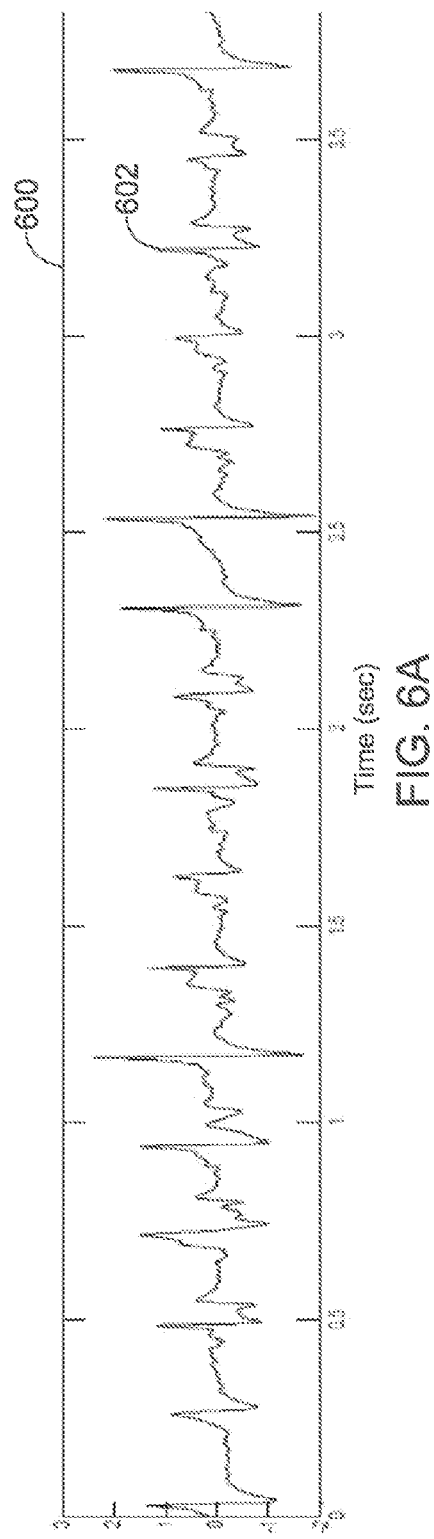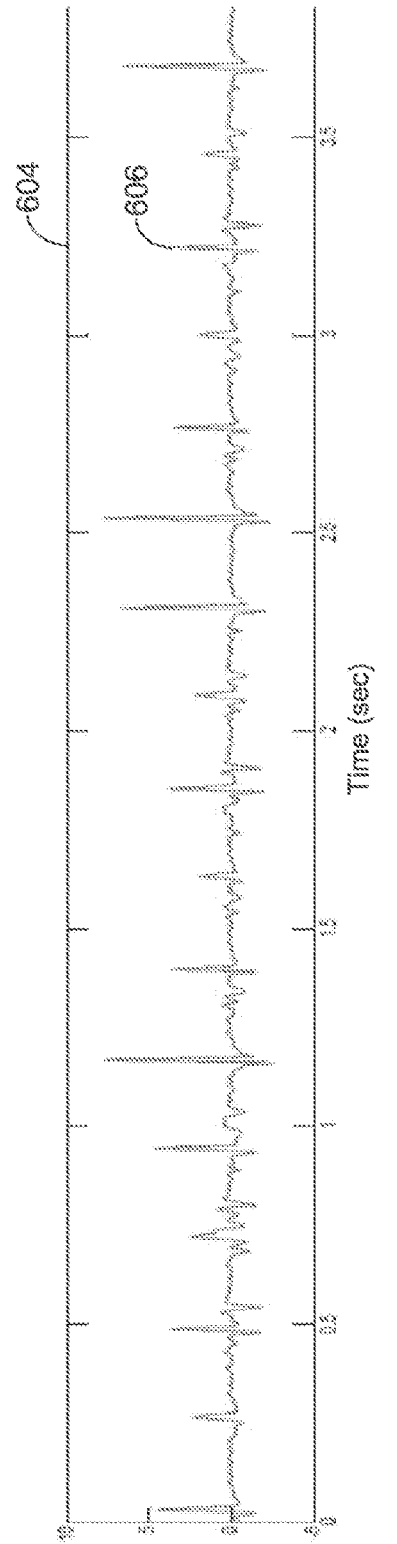

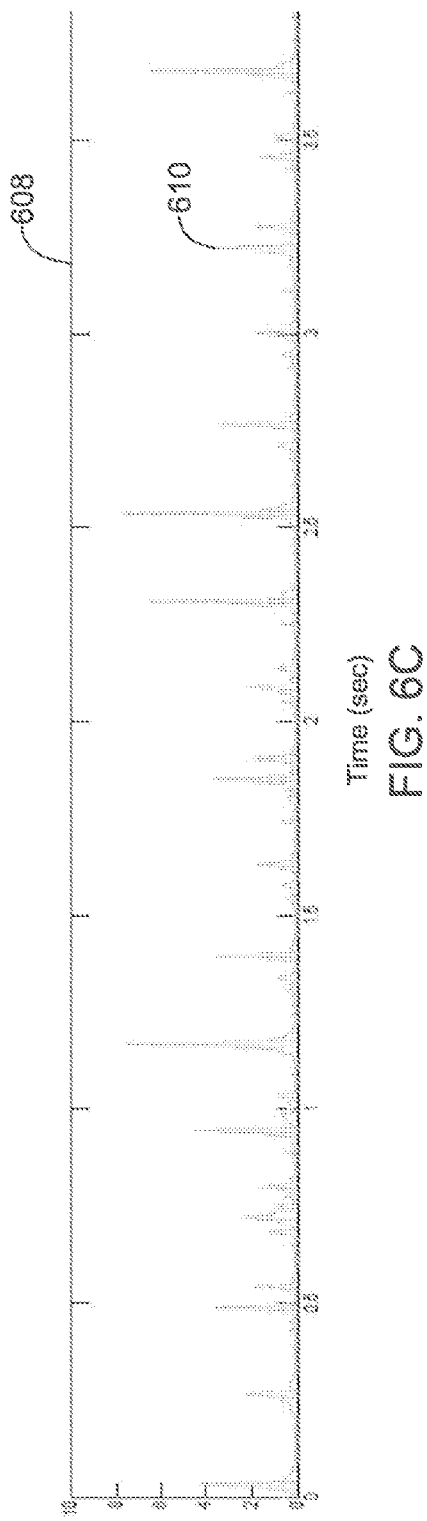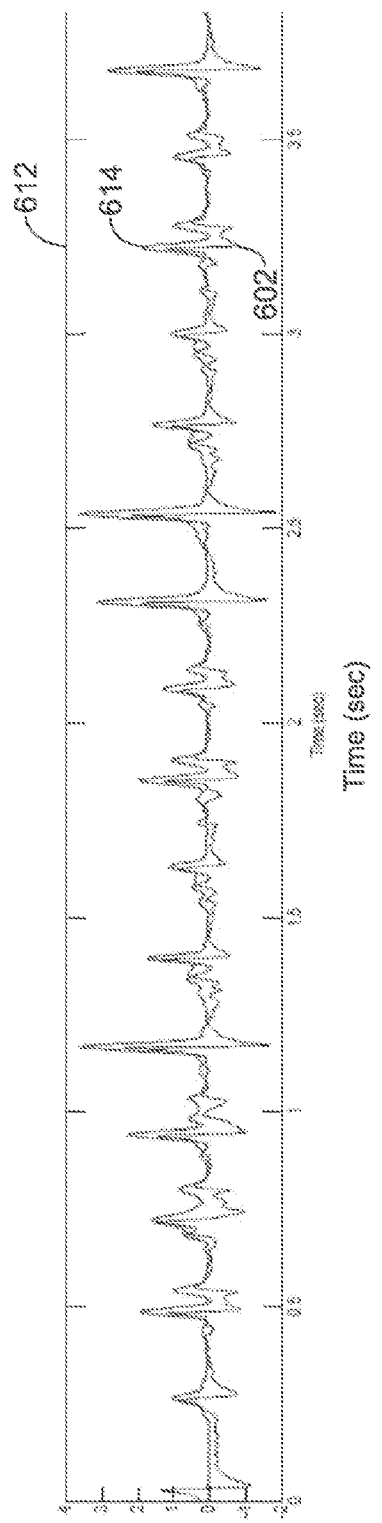

|   | 1 | 2 | 3 | 4 | 5 | 6 | 7 | 8 |
|---|---|---|---|---|---|---|---|---|
| A | ? | ? | ? | ? | ? | ? | ? | ? |
| B | 0.105 | ? | ? | ? | ? | ? | ? | ? |
| C | 0.113 | ? | ? | ? | ? | ? | ? | ? |
| D | 0.126 | ? | ? | ? | ? | ? | ? | ? |
| E | 0.135 | ? | ? | ? | ? | ? | ? | ? |
| F | 0.143 | ? | ? | ? | ? | ? | ? | ? |
| G | 0.154 | ? | ? | ? | ? | ? | ? | ? |
| H | ? | ? | 0.000 | 0.044 | 0.060 | ? | ? | 0.179 |

(Simplified representation — full matrix from FIG. 11, element 1100, with row labels A–H (Spines, 1102) and column labels 1–8 (Electrodes, 1104); many entries shown as "?")

FIG. 11

MEDICAL DEVICES FOR MAPPING CARDIAC TISSUE

CROSS-REFERENCE TO RELATED APPLICATIONS

This application claims priority under 35 U.S.C. §119 to U.S. Provisional Application Ser. No. 61/951,266, filed Mar. 11, 2014, the entirety of which is incorporated herein by reference.

TECHNICAL FIELD

The present disclosure pertains to medical devices, and methods for manufacturing medical devices. More particularly, the present disclosure pertains to medical devices and methods for mapping and/or ablating cardiac tissue.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example method of mapping electrical activity of a heart comprises sensing a plurality of signals with a plurality of electrodes positioned within the heart, separating the plurality of signals into a first group of signals and a second group of signals, and generating a data set that includes at least one known data point and one or more unknown data points, wherein the at least one known data point is generated based on the first group of signals.

Alternatively or additionally to any of the embodiments above, wherein the one or more unknown data points are generated based on the second group of signals.

Alternatively or additionally to any of the embodiments above, wherein the processing comprises one or more of the following: performing a wavelet transform on the plurality of signals, rectifying the plurality of signals, low-pass filtering the plurality of signals.

Alternatively or additionally to any of the embodiments above, wherein separating the plurality of signals into a first group of signals and a second group of signals comprises performing statistical analysis on the plurality of signals.

Alternatively or additionally to any of the embodiments above, wherein separating the plurality signals into a first group of signals and a second group of signals further comprises clustering the results of the statistical analysis, wherein the clustering produces the first group of signals and the second group of signals.

Alternatively or additionally to any of the embodiments above, wherein clustering the results of the statistical analysis comprises one of: performing a distribution-based clustering of the results of the statistical analysis, or performing a density-based clustering of the results of the statistical analysis.

Alternatively or additionally to any of the embodiments above, wherein performing a distribution-based clustering of the results of the statistical analysis comprises performing a Gaussian mixture model analysis of the results of the statistical analysis.

Alternatively or additionally to any of the embodiments above, wherein the statistical analysis comprises principal component analysis.

Another example method of identifying activation times in a plurality of signals may comprise collecting a plurality of cardiac electrical signals with a plurality of electrodes disposed within a heart, wherein each electrode collects a single cardiac electrical signal, identifying a characteristic signal from the plurality of collected cardiac electrical signals, identifying timing of one or more activation events in the characteristic signal, processing the plurality of cardiac electrical signals, clustering the plurality of cardiac electrical signals into a first cluster of signals and a second cluster of signals, wherein the first cluster of signals includes the characteristic signal, and determining an activation time for each of the cardiac electrical signals in the first cluster of signals.

Alternatively or additionally to any of the embodiments above, wherein processing the plurality of signals comprises one or more of the following: performing a wavelet transform on the plurality of signals, rectifying the plurality of signals, and low-pass filtering the plurality of signals.

Alternatively or additionally to any of the embodiments above, wherein clustering the plurality of cardiac electrical signals into a first cluster of signals and a second cluster of signals comprises: performing statistical analysis on the plurality of signals, and performing a density-based clustering of the results of the statistical analysis, wherein the results of the density-based clustering comprises the first cluster of signals and the second cluster of signals.

Alternatively or additionally to any of the embodiments above, wherein: performing statistical analysis comprises performing principal component analysis, and performing the density-based clustering comprises performing a Gaussian mixture model analysis.

Alternatively or additionally to any of the embodiments above, wherein determining activation times for each of the cardiac electrical signals in the first cluster of signals comprises: determining an activation time for the characteristic signal based on the identified timing of the one or more activation events in the characteristic signal, identifying one or more peaks in each of the other cardiac electrical signals in the first cluster of signals, identifying timings of each of the identified one or more peaks in each of the other cardiac electrical signals, and determining activation times for each of the other cardiac electrical signals based on the identified timings of the identified one or more peaks.

Alternatively or additionally to any of the embodiments above, wherein determining activation times for each of the other cardiac electrical signals based on the identified one or more peaks further comprises: removing one or more of the identified one or more peaks in each of the other cardiac electrical signals based on the identified timings of the one or more activation events in the characteristic signal, and determining activation times for each of the other cardiac electrical signals based on the remaining identified one or more peaks.

Alternatively or additionally to any of the embodiments above, may further comprise wherein determining activation times in each of the cardiac electrical signals in the first cluster of signals comprises: identifying a timing of a fiducial point in each of the signals in the first cluster of signals, determining a difference in timing between the fiducial point and one or more of the activation events in the characteristic signal, identifying timings of one or more peaks in the other cardiac electrical signals in the first cluster of signals, determining a difference in timing between the fiducial point and one or more of the identified one or more peaks in the other cardiac electrical signals in the first cluster of signals, and determining activation times based on the determined differences.

An example medical system for mapping electrical activity of a heart may comprise a catheter shaft, a plurality of electrodes coupled to the catheter shaft, a processor coupled to the catheter shaft, wherein the processor is configured to: collect a plurality of cardiac electrical signals, separating the plurality of cardiac electrical signals into a first group of signals and a second group of signals, and generating a data set that includes at least one known data point and one or more unknown data points.

Alternatively or additionally to any of the embodiments above, wherein generating a data set that includes at least one known data point and one or more unknown data points comprises: generating a known data point for each signal in the first group of signals, and generating an unknown data point for each signal in the second group of signals.

Alternatively or additionally to any of the embodiments above, further comprising identifying a characteristic signal, and identifying timing of activation events in the characteristic signal, wherein the first group of signals includes the characteristic signal.

Alternatively or additionally to any of the embodiments above, further comprising determining an activation time for the characteristic signal based on the identified timing of the activation events in the characteristic signal, identifying one or more peaks in each of the other cardiac electrical signals in the first group of signals, identifying timing of each of the identified one or more peaks in each of the other cardiac electrical signals, and determining activation times for each of the other cardiac electrical signals based on the identified timing of the identified one or more peaks.

Alternatively or additionally to any of the embodiments above, further comprising wherein the at least one known data point and the one or more unknown data points comprise activation times.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 6A is an illustration of an example cardiac electrogram;

FIG. 6B is an illustration of an example cardiac electrogram after undergoing signal processing;

FIG. 6C is another illustration of an example cardiac electrogram after undergoing signal processing;

FIG. 6D is another illustration of an example cardiac electrogram after undergoing signal processing;

FIG. 11 is an illustrative method in accordance with this disclosure that may be performed by a catheter system, such as that depicted in FIG. 1;

Figure 1:
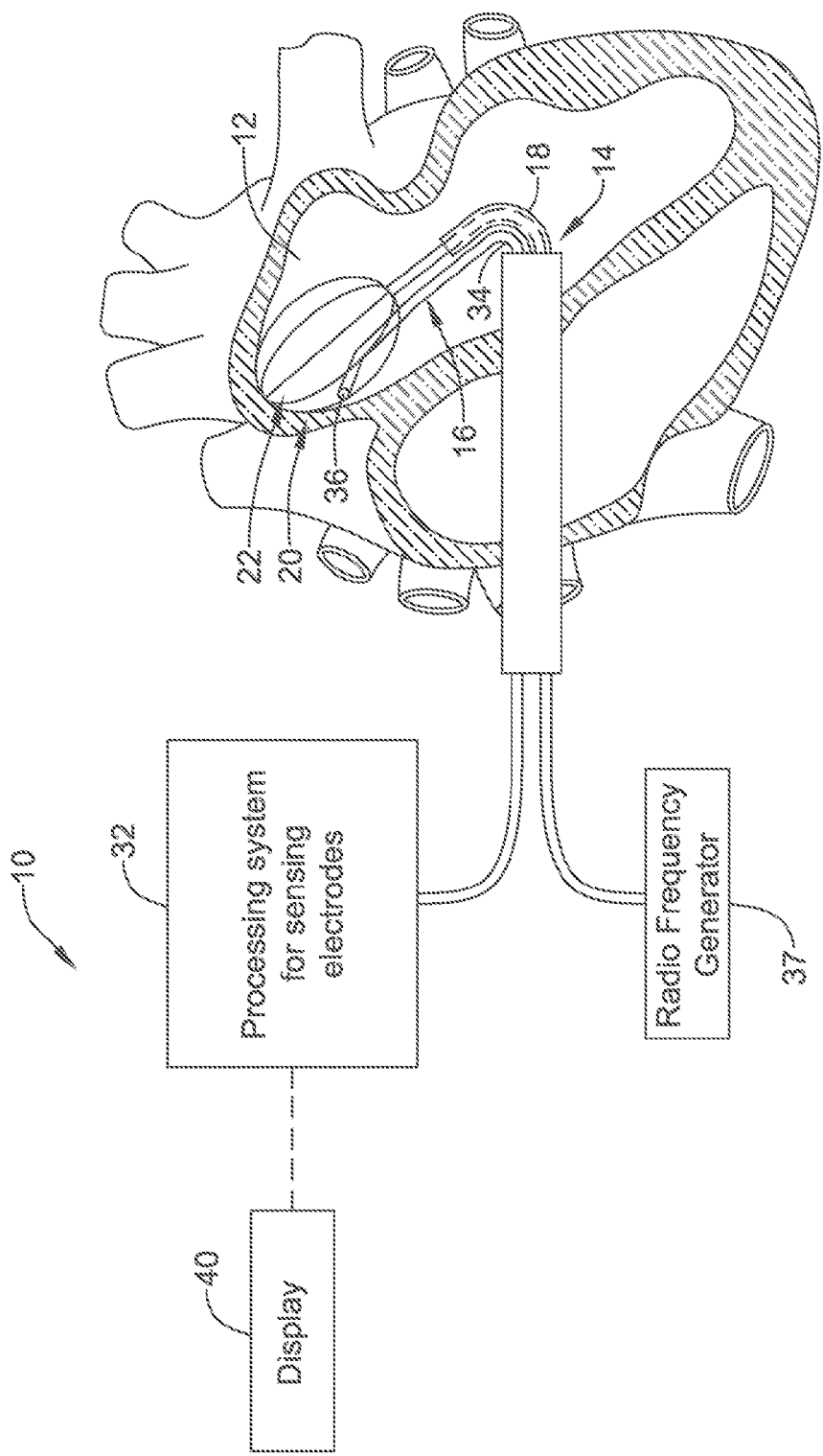
FIG. 1 is a schematic view of an example catheter system for accessing a targeted tissue region in the body for diagnostic and therapeutic purposes.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an example", "some examples", "other examples", etc., indicate that the example described may include one or more particular features, structures, and/or characteristics. However, such recitations do not necessarily mean that all examples include the particular features, structures, and/or characteristics. Additionally, when particular features, structures, and/or characteristics are described in connection with one example, it should be understood that such features, structures, and/or characteristics may also be used connection with other examples whether or not explicitly described unless clearly stated to the contrary. Also, when particular features, structures, and/or characteristics are described in connection with one example, it is implicit that other examples may include less than all of the disclosed features, structures, and/or characteristics in all combinations.

The following detailed description should be read with reference to the drawings in which similar elements in different drawings are numbered the same. The drawings, which are not necessarily to scale, depict illustrative embodiments and are not intended to limit the scope of the invention.

Mapping the electrophysiology of heart rhythm disorders often involves the introduction of a constellation catheter or other mapping/sensing device having a plurality of electrodes and/or sensors (e.g., CONSTELLATION®, commercially available from Boston Scientific) into a cardiac chamber. The sensors, for example electrodes, detect cardiac electrical activity at sensor locations. It may be desirable to have the cardiac electrical activity processed into electrogram signals that accurately represent cellular excitation through cardiac tissue relative to the sensor locations. A processing system may then analyze and output the signal to a display device. Further, the processing system may output the signal as an activation or vector field map. A user, such as a physician, may use the activation or vector field map to perform a diagnostic procedure.

Some example catheters may include sixty-four or more electrodes which each detect cardiac electrical activity. Accordingly, the processing system may process each of the sixty-four or more detected cardiac electrical activity signals into electrogram signals. In some examples, a user may then input information for each of the sixty-four or more electrogram signals which the processing system uses in determining pieces of data to populate an activation map. This inputting of information for such a high number of electrogram signals can result in lengthy procedure times. The methods and systems disclosed herein are designed to reduce the amount of information a user needs to input for the processing system to determine pieces of data to populate an activation map. For example, some of the methods disclosed herein may reduce the number of electrogram signals for which a user needs to input information or suggest information to a user for review for at least some of the electrogram signals. Other methods and medical devices are also disclosed.

FIG. 1 is a schematic view of a system 10 for accessing a targeted tissue region in the body for diagnostic and/or therapeutic purposes. FIG. 1 generally shows the system 10 deployed in the left atrium of the heart. Alternatively, system 10 can be deployed in other regions of the heart, such as the left ventricle, right atrium, or right ventricle. While the illustrated embodiment shows system 10 being used for ablating myocardial tissue, system 10 (and the methods described herein) may alternatively be configured for use in other tissue ablation applications, such as procedures for ablating tissue in the prostrate, brain, gall bladder, uterus, nerves, blood vessels and other regions of the body, including in systems that are not necessarily catheter-based.

System 10 includes mapping probe 14 and ablation probe 16. Each probe 14/16 may be separately introduced into the selected heart region 12 through a vein or artery (e.g., the femoral vein or artery) using a suitable percutaneous access technique. Alternatively, mapping probe 14 and ablation probe 16 can be assembled in an integrated structure for simultaneous introduction and deployment in the heart region 12.

Mapping probe 14 may include flexible catheter body 18. The distal end of catheter body 18 carries three-dimensional multiple electrode structure 20. In the illustrated embodiment, structure 20 takes the form of a basket defining an open interior space 22 (see FIG. 2), although other multiple electrode structures could be used. Structure 20 carries a plurality of mapping electrodes 24 (not explicitly shown on FIG. 1, but shown on FIG. 2) each having an electrode location on structure 20 and a conductive member. Each electrode 24 may be configured to sense or detect intrinsic physiological activity in an anatomical region adjacent to each electrode 24.

In some examples, electrodes 24 may be configured to detect activation signals of the intrinsic physiological activity within the anatomical structure. For example, intrinsic cardiac electrical activity may comprise repeating or semi-repeating waves of electrical activity with relatively large spikes in activity at the beginning of activation events. Electrodes 24 may sense such activation events and the times at which such activation events occur. Generally, electrodes 24 may sense activation events at different times as an electrical activity wave propagates through the heart. For instance, an electrical wave may begin near a first group of electrodes 24, which may sense an activation event at relatively the same time or within a relatively small window of time. As the electrical wave propagates through the heart, a second group of electrodes 24 may sense the activation even of the electrical wave at times later than the first group of electrodes 24.

Electrodes 24 are electrically coupled to processing system 32. A signal wire (not shown) may be electrically coupled to each electrode 24 on structure 20. The signal wires may extend through body 18 of probe 14 and electrically couple each electrode 24 to an input of processing system 32. Electrodes 24 sense cardiac electrical activity in the anatomical region, e.g., myocardial tissue, adjacent to their physical location within the heart. The sensed cardiac electrical activity (e.g., electrical signals generated by the heart which may include activation signals) may be processed by processing system 32 to assist a user, for example a physician, by generating an anatomical map (e.g., a vector field map, an activation time map) to identify one or more sites within the heart appropriate for a diagnostic and/or treatment procedure, such as an ablation procedure. For example, processing system 32 may identify a near-field signal component (e.g., activation signals originating from cellular tissue adjacent to mapping electrodes 24) or an obstructive far-field signal component (e.g., activation signals originating from non-adjacent tissue). In such examples where structure 20 is disposed in an atrium of the heart, as in FIG. 1, the near-field signal component may include activation signals originating from atrial myocardial tissue whereas the far-field signal component may include activation signals originating from ventricular myocardial tissue. The near-field activation signal component may be further analyzed to find the presence of a pathology and to determine a location suitable for ablation for treatment of the pathology (e.g., ablation therapy).

Processing system 32 may include dedicated circuitry (e.g., discrete logic elements and one or more microcontrollers; application-specific integrated circuits (ASICs); or specially configured programmable devices, such as, for example, programmable logic devices (PLDs) or field programmable gate arrays (FPGAs)) for receiving and/or processing the acquired cardiac electrical activity. In some examples, processing system 32 includes a general purpose microprocessor and/or a specialized microprocessor (e.g., a digital signal processor, or DSP, which may be optimized for processing activation signals) that executes instructions to receive, analyze and display information associated with the received cardiac electrical activity. In such examples, processing system 32 can include program instructions, which when executed, perform part of the signal processing. Program instructions can include, for example, firmware, microcode or application code that is executed by microprocessors or microcontrollers. The above-mentioned implementations are merely exemplary, and the reader will appreciate that processing system 32 can take any suitable form for receiving electrical signals and processing the received electrical signals.

In some examples, processing system 32 may be configured to measure the sensed cardiac electrical activity in the myocardial tissue adjacent to electrodes 24. For example, processing system 32 may be configured to detect cardiac electrical activity associated with a dominant rotor or divergent activation pattern in the anatomical feature being mapped. Dominant rotors and/or divergent activation patterns may have a role in the initiation and maintenance of atrial fibrillation, and ablation of the rotor path, rotor core, and/or divergent foci may be effective in terminating the atrial fibrillation. Processing system 32 processes the sensed cardiac electrical activity to generate a display of relevant characteristics, such as an isochronal map, activation time map, action potential duration (APD) map, a vector field map, a contour map, a reliability map, an electrogram, a cardiac action potential and the like. The relevant characteristics may assist a user to identify a site suitable for ablation therapy.

Ablation probe 16 includes flexible catheter body 34 that carries one or more ablation electrodes 36. The one or more ablation electrodes 36 are electrically connected to radio frequency (RF) generator 37 that is configured to deliver ablation energy to the one or more ablation electrodes 36. Ablation probe 16 may be movable with respect to the anatomical feature to be treated, as well as structure 20. Ablation probe 16 may be positionable between or adjacent to electrodes 24 of structure 20 as the one or more ablation electrodes 36 are positioned with respect to the tissue to be treated.

Processing system 32 may output data to a suitable device, for example display device 40, which may display relevant information for a user. In some examples, device 40 is a CRT, LED, or other type of display, or a printer. Device 40 presents the relevant characteristics in a format useful to the user. In addition, processing system 32 may generate position-identifying output for display on device 40 that aids the user in guiding ablation electrode(s) 36 into contact with tissue at the site identified for ablation.

Figure 2:
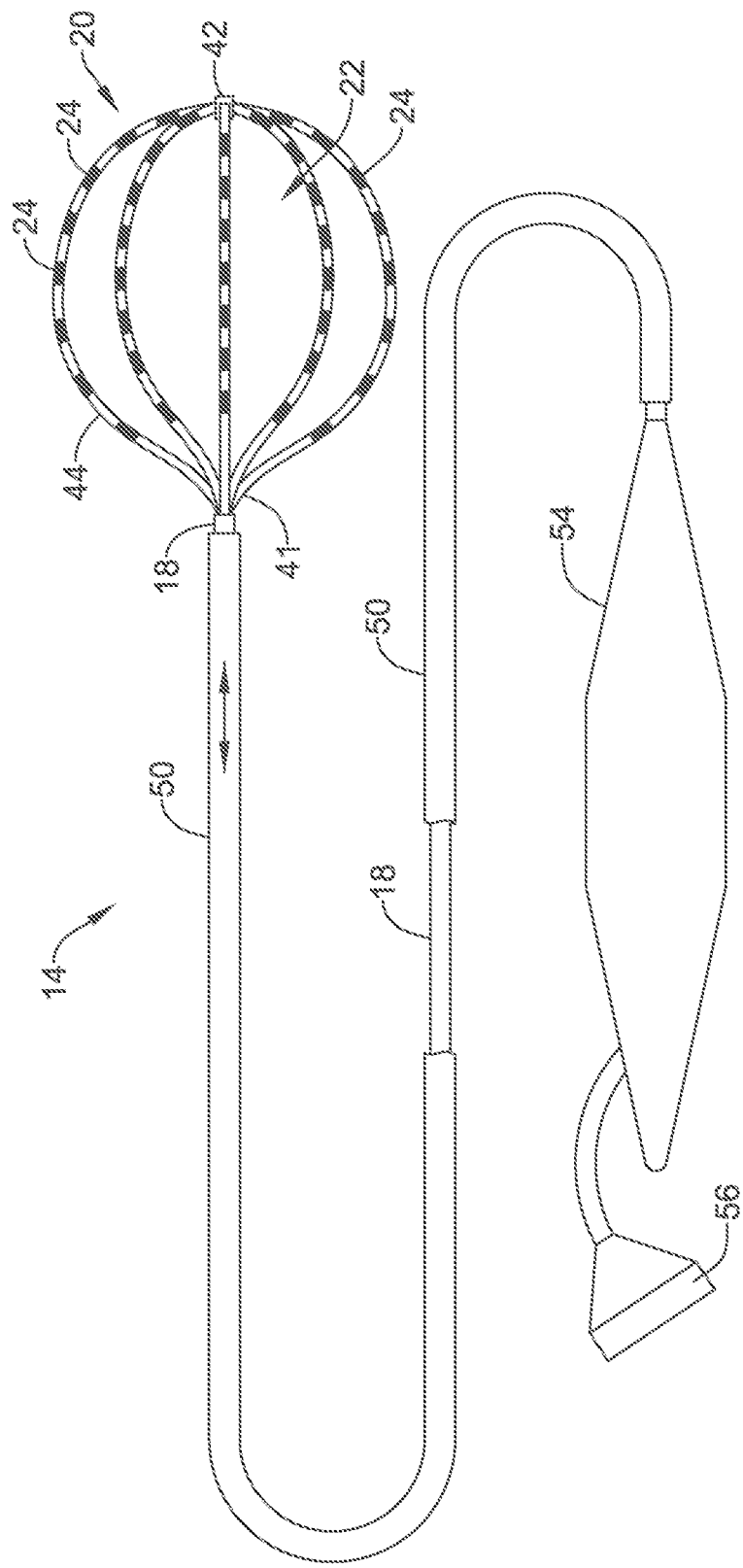
FIG. 2 is a schematic view of an example mapping catheter having a basket functional element carrying structure for use in association with the system of FIG. 1.

FIG. 2 illustrates mapping catheter 14 and shows electrodes 24 at the distal end suitable for use in system 10 shown in FIG. 1. Mapping catheter 14 may include flexible catheter body 18, the distal end of which may carry three-dimensional multiple electrode structure 20 with mapping electrodes or sensors 24. Mapping electrodes 24 may sense cardiac electrical activity, including activation signals, in the myocardial tissue. The sensed cardiac electrical activity may be processed by the processing system 32 to assist a user in identifying the site or sites having a heart rhythm disorder or other myocardial pathology via generated and displayed relevant characteristics. This information can then be used to determine an appropriate location for applying appropriate therapy, such as ablation, to the identified sites, and to navigate the one or more ablation electrodes 36 to the identified sites.

The illustrated three-dimensional multiple electrode structure 20 comprises base member 41 and end cap 42 between which flexible splines 44 generally extend in a circumferentially spaced relationship. As discussed herein, structure 20 may take the form of a basket defining an open interior space 22. In some examples, the splines 44 are made of a resilient inert material, such as Nitinol, other metals, silicone rubber, suitable polymers, or the like and are connected between base member 41 and end cap 42 in a resilient, pretensioned condition, to bend and conform to the tissue surface they contact. In the example illustrated in FIG. 2, eight splines 44 form three dimensional multiple electrode structure 20. Additional or fewer splines 44 could be used in other examples. As illustrated, each spline 44 carries eight mapping electrodes 24. Additional or fewer mapping electrodes 24 could be disposed on each spline 44 in other examples of three dimensional multiple electrode structure 20. In the example illustrated in FIG. 2, structure 20 is relatively small (e.g., 40 mm or less in diameter). In alternative examples, structure 20 is even smaller or larger (e.g., less than or greater than 40 mm in diameter).

Slidable sheath 50 may be movable along the major axis of catheter body 18. Moving sheath 50 distally relative to catheter body 18 may cause sheath 50 to move over structure 20, thereby collapsing structure 20 into a compact, low profile condition suitable for introduction into and/or removal from an interior space of an anatomical structure, such as, for example, the heart. In contrast, moving sheath 50 proximally relative to the catheter body may expose structure 20, allowing structure 20 to elastically expand and assume the pretensed position illustrated in FIG. 2.

A signal wire (not shown) may be electrically coupled to each mapping electrode 24. The signal wires may extend through body 18 of mapping catheter 20 (or otherwise through and/or along body 18) into handle 54, in which they are coupled to external connector 56, which may be a multiple pin connector. Connector 56 electrically couples mapping electrodes 24 to processing system 32. It should be understood that these descriptions are just examples. Some addition details regarding these and other example mapping systems and methods for processing signals generated by a mapping catheter can be found in U.S. Pat. Nos. 6,070,094, 6,233,491, and 6,735,465, the disclosures of which are hereby expressly incorporated herein by reference.

Figure 3:
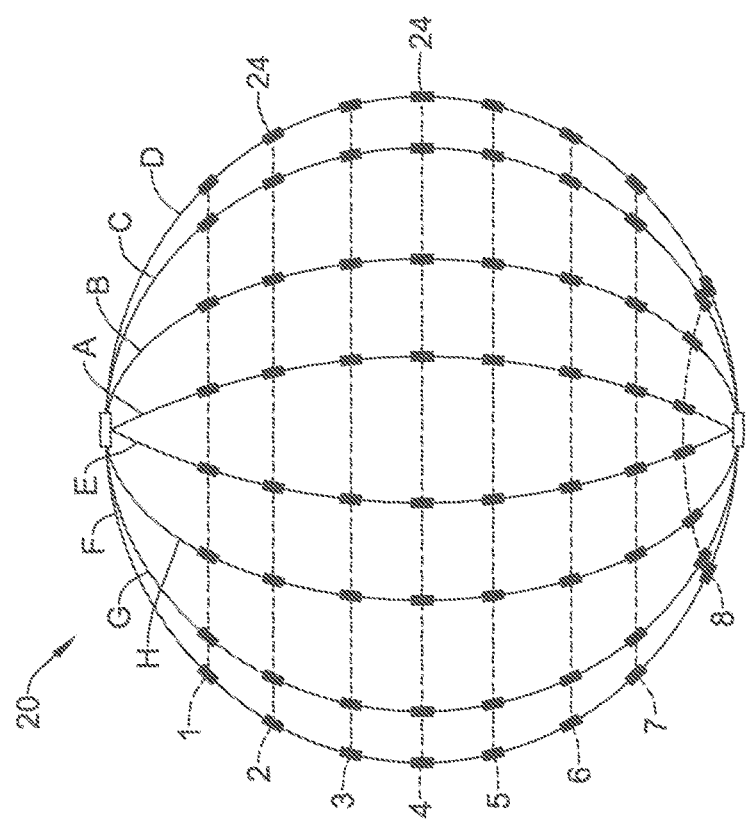
FIG. 3 is a schematic view of an example functional element including a plurality of mapping electrodes.

To illustrate the operation of system 10, FIG. 3 is a schematic side view of an example of basket structure 20 including a plurality of mapping electrodes 24. In the illustrated example, the basket structure includes 64 mapping electrodes 24. Mapping electrodes 24 are disposed in groups of eight electrodes (labeled 1, 2, 3, 4, 5, 6, 7, and 8) on each of eight splines (labeled A, B, C, D, E, F, G, and H). While an arrangement of sixty-four mapping electrodes 24 is shown disposed on basket structure 20, mapping electrodes 24 may alternatively be arranged in different numbers (more or fewer splines and/or electrodes), on different structures, and/or in different positions. In addition, multiple basket structures can be deployed in the same or different anatomical structures to simultaneously obtain signals from different anatomical structures.

After basket structure 20 is positioned adjacent to the anatomical structure to be treated (e.g. left atrium, left ventricle, right atrium, or right ventricle of the heart), processing system 32 is configured to record the cardiac electrical activity from each electrode 24 channel, and the cardiac electrical activity is related to physiological activity of the adjacent anatomical structure. For instance, cardiac electrical activity may include activation signals which may indicate an onset of physiological activity, such as a contraction of the heart. Electrodes 24 sense such cardiac electrical activity which includes activation signals. The cardiac electrical activity of physiological activity may be sensed in response to intrinsic physiological activity (e.g. intrinsically generated electrical signals) or based on a predetermined pacing protocol instituted by at least one of the plurality of electrodes 24 (e.g. delivered electrical signals delivered by a pacing device).

The arrangement, size, spacing and location of electrodes along a constellation catheter or other mapping/sensing device, in combination with the specific geometry of the targeted anatomical structure, may contribute to the ability (or inability) of electrodes 24 to sense, measure, collect and transmit electrical activity of cellular tissue. As stated, because splines 44 of a mapping catheter, constellation catheter or other similar sensing device are bendable, they may conform to a specific anatomical region in a variety of shapes and/or configurations. Further, at any given position in the anatomical region, structure 20 may be manipulated such that one or more splines 44 may not contact adjacent cellular tissue. For example, splines 44 may twist, bend, or lie atop one another, thereby separating splines 44 from nearby cellular tissue. Additionally, because electrodes 24 are disposed on one or more of splines 44, they also may not maintain contact with adjacent cellular tissue. Electrodes 24 that do not maintain contact with cellular tissue may be incapable of sensing, detecting, measuring, collecting and/or transmitting electrical activity information. Further, because electrodes 24 may be incapable of sensing, detecting, measuring, collecting and/or transmitting electrical activity information, processing system 32 may be incapable of accurately displaying diagnostic information. For example, some necessary information may be missing and/or displayed inaccurately.

In addition to that stated above, electrodes 24 may not be in contact with adjacent cellular tissue for other reasons. For example, manipulation of mapping catheter 14 may result in movement of electrodes 24, thereby creating poor electrode-to-tissue contact. Further, electrodes 24 may be positioned adjacent fibrous, dead or functionally refractory tissue. Electrodes 24 positioned adjacent fibrous, dead or functionally refractory tissue may not be able to sense changes in electrical potential because fibrous, dead or functionally refractory tissue may be incapable of depolarizing and/or responding to changes in electrical potential. Finally, far-field ventricular events and electrical line noise may distort measurement of tissue activity.

However, electrodes 24 that contact healthy, responsive cellular tissue may sense cardiac electrical activity such as a change in the voltage potential of a propagating cellular activation wavefront. Further, in a normal functioning heart, electrical discharge of the myocardial cells may occur in a systematic, linear fashion. Therefore, detection of non-linear propagation of the cellular excitation wavefront may be indicative of cellular firing in an abnormal fashion. For example, cellular firing in a rotating pattern may indicate the presence of dominant rotors and/or divergent activation patterns. Further, because the presence of the abnormal cellular firing may occur over localized target tissue regions, it is possible that electrical activity may change form, strength or direction when propagating around, within, among or adjacent to diseased or abnormal cellular tissue. Identification of these localized areas of diseased or abnormal tissue may provide a user with a location for which to perform a therapeutic and/or diagnostic procedure. For example, identification of an area including reentrant or rotor currents may be indicative of an area of diseased or abnormal cellular tissue. The diseased or abnormal cellular tissue may be targeted for an ablative procedure. An activation time map may be used to identify areas of circular, adherent, rotor or other abnormal cellular excitation wavefront propagation.

As described previously, in order to generate an activation time map, processing system may need to receive input from a user. For example, after sensing cardiac electrical activity at each electrode 24, processing system 32 may display the sensed cardiac electrical activity at display 40 as an electrogram. A user may then input information associated with each electrogram, and processing system 32 may use this input information to generate the activation time map. However, requiring a user to input information for each electrogram may be time consuming. Accordingly, one or more techniques described herein may reduce the number of electrograms for which processing system 32 needs a user to input information, and/or generate suggested input information.

Figure 4:
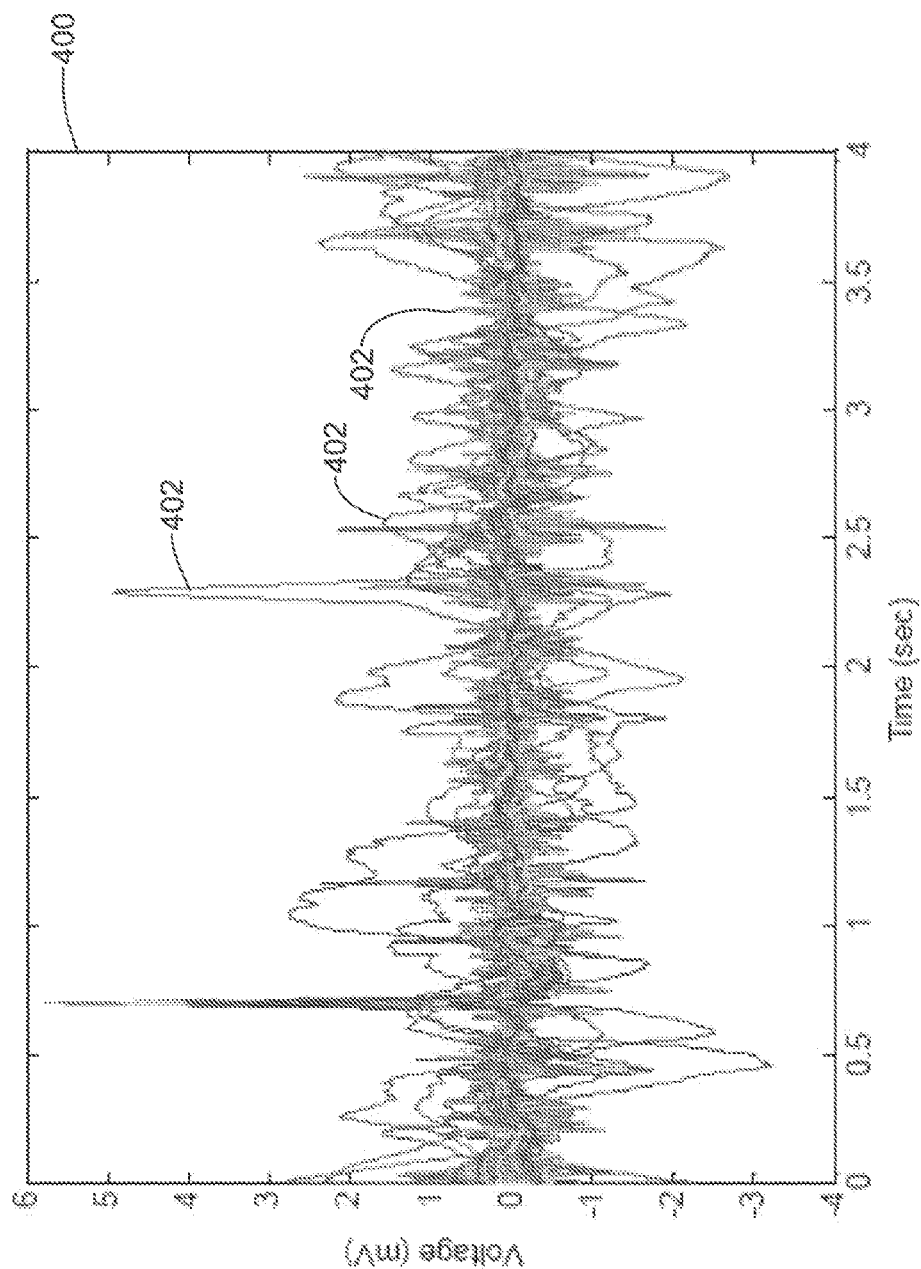
FIG. 4 is an illustration of sensed cardiac electrical signals.

In some examples, after collecting cardiac electrical activity sensed by electrodes 24, processing system 32 may generate a number of electrograms based on the sensed cardiac electrical activity equal to the number of electrodes of the system. Processing system may additionally display the generated electrograms, for example at display device 40. In some examples, the electrograms may simply be the raw sensed cardiac electrical activity. Processing system 32 may display each electrogram in a single graphical display, with all of the electrograms overlapping. Graph 400 in FIG. 4 displays signals 402 in such a fashion. In other examples, processing system 32 may display each electrogram in a separate graph. Displaying such electrograms may allow a user to assess the quality of the sensed cardiac electrical activity. For example, normal cardiac electrical activity appears as a noticeable, repeating waveform. Abnormal looking cardiac electrical activity may indicate problems with the electrodes—for example the electrodes may not be in good electrical contact with the tissue. Using such abnormal electrograms to generate an activation time map may result in an inaccurate activation time map, which if used in ablation therapy could result in ineffective or even harmful therapy. Accordingly, if a user determines that the sensed cardiac electrical activity are abnormal, the user may reposition electrodes 24 and instruct processing system 32 to again collect cardiac electrical activity for each electrode. In some examples, each electrogram may span one to four seconds and are stored in a memory of processing system 32.

In at least some examples, processing system 32 may identify a characteristic signal. A characteristic signal may be one of the electrograms which display characteristics of a normal electrogram, e.g. a series of obvious repeating or semi-repeating peaks and valleys. Such features may indicate that the electrode associated with the characteristic signal is in good electrical contact with the tissue. Processing system 32 may identify a characteristic signal by comparing each electrogram to a reference electrogram and generating a difference score, for example using one or more statistical techniques for indicating how similar each electrogram is to the reference electrogram. Processing system 32 may identify the electrogram with the highest score—that is, the most similar to the reference electrogram—as the characteristic signal. In other examples, processing system may use other techniques for identifying a characteristic electrogram. In still other examples, a user may select one of the electrograms as the characteristic signal. For example, processing system 32 may display each electrogram, and the user may select one of the displayed electrogram at display device 40 using a peripheral input device, e.g. a keyboard or mouse, or through touch input if display device 40 is a touch-sensitive display device. Alternatively, processing system 32 may identify one of the electrograms as an initial characteristic signal and may display the initial characteristic signal at display device 40. A user may then enter input either confirming the initial characteristic signal as the characteristic signal or selecting a different electrogram as the characteristic signal.

Figure 5:
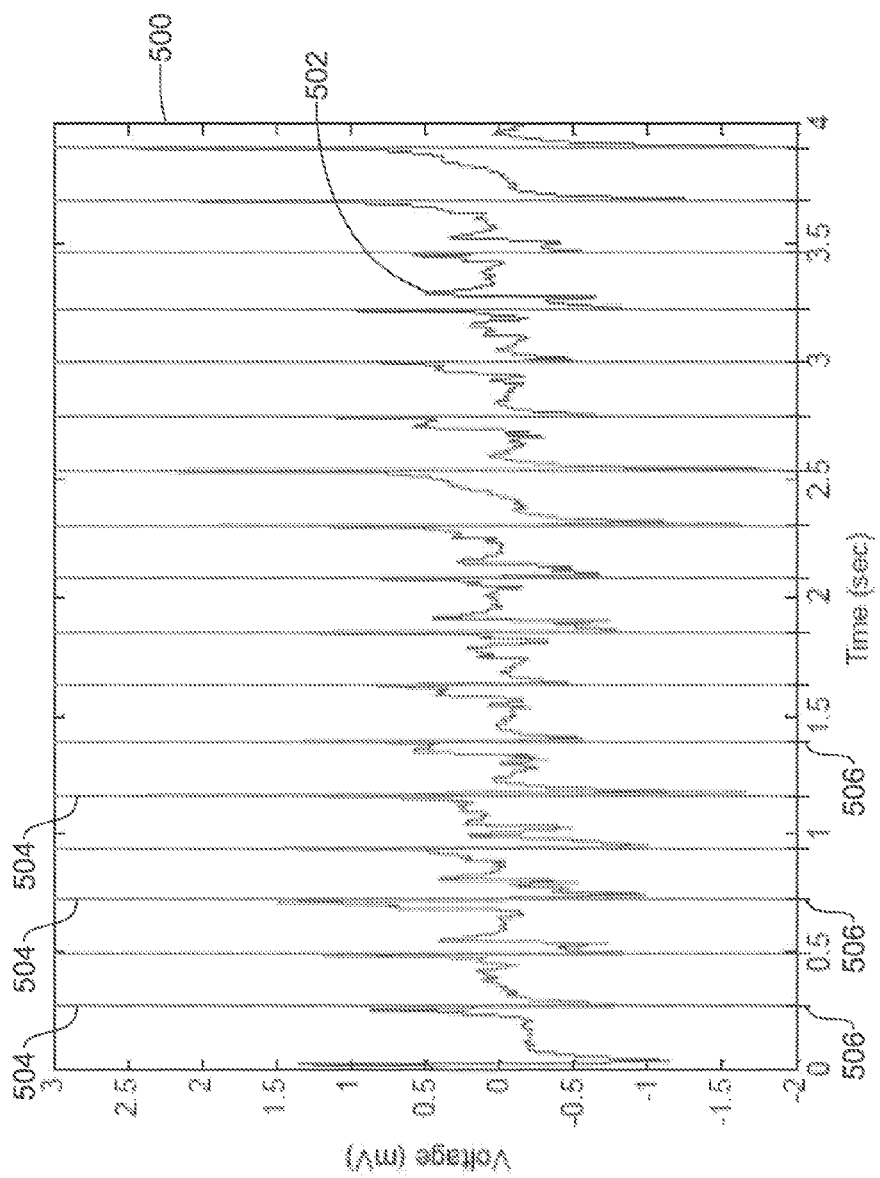
FIG. 5 is an illustration of an example characteristic electrogram, which is one of a plurality of sensed cardiac electrical signals.

After identifying or determining a characteristic signal, processing system 32 may identify activation events and timings of any identified activation events in the characteristic signal. For example, processing system 32 may determine a derivative of the characteristic signal and identify locations within the derivative of the characteristic signal that are less than a predetermined threshold as activation events. In other examples, processing system 32 may user other techniques for identifying activation events in the characteristic signal. For instance, processing system 32 may employ a peak finding algorithm and determine that any identified peaks are activation events. In other examples, processing system 32 may display the characteristic signal at display device 40 and a user may select one or more locations in the characteristic signal as activation events. In still other examples, processing system 32 may identify one or more activation events and display the characteristic signal and determined activation events at display device 40. A user may modify the activation events identified by processing system 32, for example by removing identified activation events, adding activation events, and/or moving identified activation events. In any case, processing system 32 may additionally record the timings of the identified activation events. FIG. 5 displays an example result of identifying activation events and activation event timings. For instance, graph 500 includes example characteristic signal 502 along with identified activation events 504 and activation event timings 506.

Processing system 32 may additionally process each of the electrograms, as depicted in FIGS. 6A-6D. FIG. 6A depicts graph 600 which includes example electrogram 602. Processing system 32 may utilize one or more signal processing techniques to transform example electrogram 602 to minimize or remove particular features. In some examples, processing system 32 may perform a wavelet transform on example electrogram 602. Any number of wavelet transforms may be used. In at least some examples the wavelet transform is a Haar wavelet transform. FIG. 6B depicts graph 604 which includes example electrogram 606, where example electrogram 606 represents example electrogram 602 after processing using a Haar wavelet transform.

In some examples, processing system 32 may additionally rectify example electrogram 606. FIG. 6C illustrates graph 608 which depicts example electrogram 610. Example electrogram 610 is a depiction of example electrogram 606 after processing system performs rectification of example electrogram 606.

In additional examples, processing system 32 may further generate a power envelope of example electrogram 610. For example, processing system 32 may perform a low-pass filtering of example electrogram 610. In other examples, processing system 32 may utilize other techniques for generating a power envelope. FIG. 6D depicts graph 612 including example electrogram 614, which represents example electrogram 610 after processing system 32 processes example electrogram 610 to generate a power envelope. Graph 612 additionally depicts example electrogram 602 overlaid on example electrogram 614 as a comparison of the original electrogram to the fully processed electrogram.

Although the above description described a technique for processing electrograms using multiple signal processing techniques, in other examples, only one or two of the processing techniques may be used. For example, processing the electrograms may only consist of performing a wavelet transform on the electrogram. In other examples, the processing may only consist of rectification. In still other examples, the processing may only consist of generating a power envelope. In yet other examples, any combination of two of these processes may be combined to perform processing on the electrogram. It is also noted that these processing techniques should not be viewed as limiting. In other examples, processing system 32 may use other and/or additional signal processing techniques to process the electrogram. Additionally, the above described process has been described with respect to a single electrogram, however, in practice, processing system 32 may perform similar processing techniques on each of the electrograms generated from each electrode 24.

Figure 7:
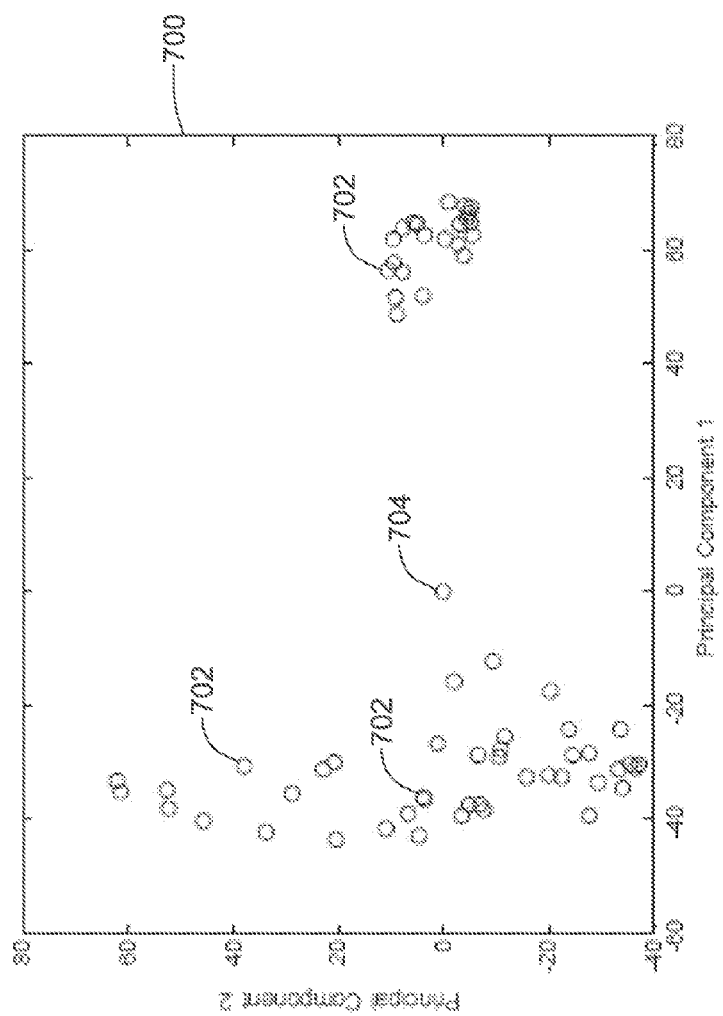
FIG. 7 is an illustration of a result of performing a statistical analysis on a plurality of sensed cardiac electrical signals.

After processing each of the electrograms, processing system 32 may additionally perform a statistical analysis on all of the processed electrograms. In some examples, processing system 32 may perform a cross correlation analysis between the characteristic signal and the processed electrograms. In other examples, processing system 32 may perform a Linear Discriminant Analysis on the processed electrograms. In at least some examples, processing system 32 may perform a principal component analysis on the processed electrograms. FIG. 7 depicts graph 700, which includes data points 702, and depicts the results of a principal component analysis on the sixty-four processed electrograms. Graph 700 also includes zero-point 704, which merely indicates the (0,0) point on graph 700. Each data point 702 represents one of the processed electrograms graphed with respect to a first principal component and a second principal component. In other examples, processing system 32 may transform the processed electrograms utilizing other statistical analysis techniques common in exploratory data analysis. In still other examples, processing system 32 may employ multiple statistical analysis techniques to analyze the processed electrograms.

Figure 8:
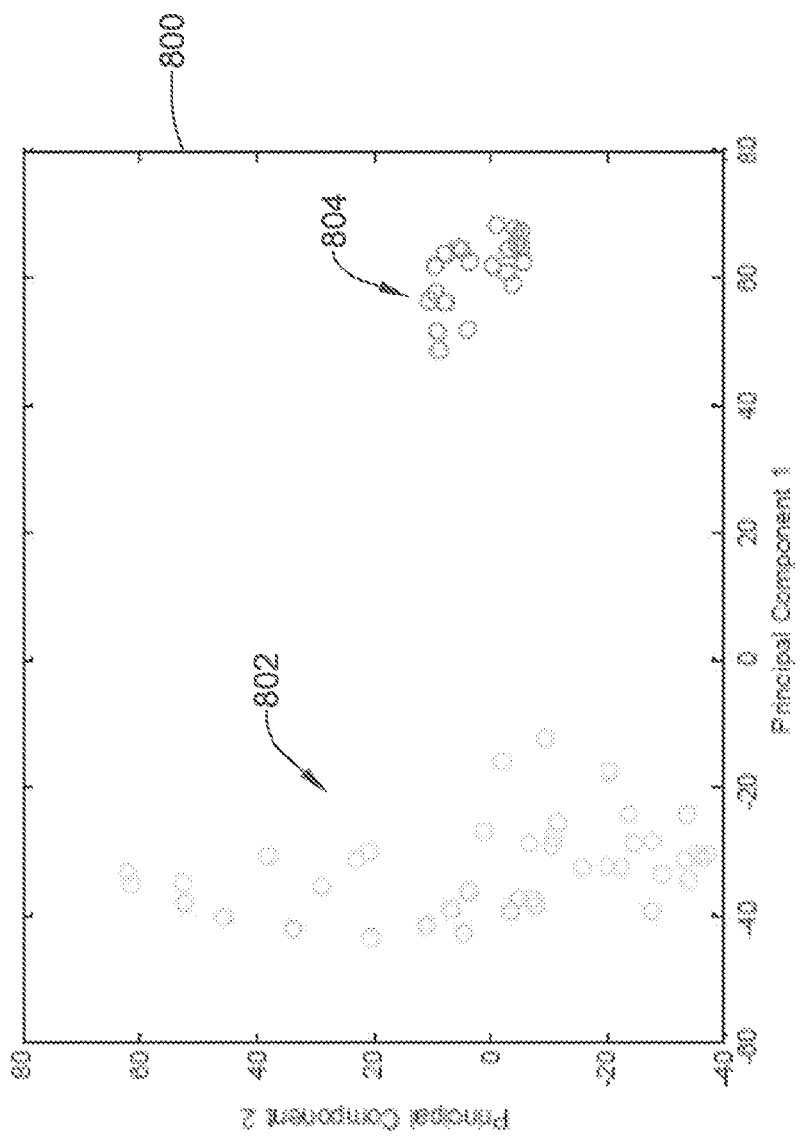
FIG. 8 is another illustration of a result of performing a statistical analysis on a plurality of sensed cardiac electrical signals.

Once processing system 32 has completed the statistical transformations of the processed electrograms, processing system 32 may cluster the results of the statistical transform. For example, processing system 32 may separate the results into multiple separate groups or clusters. In general, this clustering processing may identify groups of electrograms which are similar to one another, or on the basis of certain features within each electrogram. In some examples, processing system 32 may perform a density-based clustering technique in order to group or cluster the results of the statistical transform. In other examples, processing system 32 may perform a distribution-based clustering technique in order to group or cluster the results of the statistical transform. More specifically, in some examples where processing system 32 uses a distribution-based clustering technique, processing system 32 may perform a Gaussian mixture model (GMM) analysis on the results of the statistical transform. In at least some examples, the GMM analysis may be a two-dimensional analysis, and the results of the GMM analysis may be two separate groups or clusters of electrograms. FIG. 8 depicts graph 800 including results of a two-dimensional GMM analysis. Electrogram groups 802 and 804 represent the output of the GMM analysis. In general, processing system 32 may use any of a number of known clustering techniques (such as the ones described above, or others known in the art, for example k-means clustering) for separating the electrograms into two or more groups or clusters.

In some examples, the clustering process may produce more than two groups or clusters of electrograms. For example, in a GMM analysis, a user may select a specific number of groups or clusters as output of the GMM analysis. Accordingly, in examples where a user selects three groups or clusters, the output of the GMM analysis is three groups or clusters. However, in other examples, a user may select any number of groups or clusters. Selecting more than two groups or clusters may be advantageous in situations where the results of the statistical processing do not produce clear distinctions between electrograms.

In any event, one of the groups of electrograms contains the characteristic signal. In the example of FIG. 8, electrogram group 802 contains the characteristic signal. This disclosure generally refers to electrogram group 802, which contains the characteristic signal, as the "first group" and electrogram group 804 as the "second group." In examples where the output of the GMM analysis is more than two groups, the "second group" may consist of two or more subgroups. For example, the "first group" may still be the group or cluster of electrograms that contains the characteristic signal. The "second group," however, may consist of all other groups or clusters that do not contain the characteristic signal. Ultimately, when populating an activation time map, one or more of the known data points may be generated from one or more of the electrograms in the first group. Additionally, one or more of the unknown data points may be generated from the second group. In other examples, a known data point may be generated from each electrogram in the first group and an unknown data point may be generated from each electrogram in the second group.

In some examples, performing a clustering process may begin with one or more estimated or guessed parameters, and different parameters may produce different results. For example, using a first set of parameters may end in a result that is a local minimum. Using a second set of parameters may also end in a result that is a local minimum, but the local minimum is a lower minimum that the local minimum using the first set of parameters. Accordingly, in order to determine a global minimum, that is a local minimum that is lowest of all local minimum, processing system 32 may perform the clustering process multiple times. In some examples, processing system 32 may perform the clustering process 25, 40, 50, or any other suitable number of times. Processing system 32 may then use the results with the lowest overall local minimum as the results of the clustering process—e.g. the groupings resulting from the clustering process resulting in the lowest overall local minimum.

In other examples, a user may not identify a characteristic signal. In such examples, processing system 32 may determine which group or cluster of electrograms is the "first group" and which group(s) or cluster(s) are the "second group." For instance, after performing a statistical analysis, such as principal component analysis or other appropriate statistical processing techniques, processing system 32 may further test electrogram characteristics of each group. For example, processing system 32 may perform an organizational index calculation on the fast-fourier transform (FFT) of each electrogram within each group or cluster. Then, processing system 32 may determine the group or cluster which shows the greatest amount of organization in the FFTs of the electrograms as the "first group" and all of the other groups as part of the "second group."

Once processing system 32 has separated the electrograms into at least a first and a second group, processing system 32 may additionally determine activation times for populating an activation time map. In some examples, processing system 32 may determine an activation time from the characteristic signal in a slightly different manner from the other electrograms in the first group. For example, processing system 32 already has stored in memory timings of activation events for the characteristic signal. Processing system may then identify one or more fiducial points in the characteristic signal. For example, one of the electrograms may be a reference electrogram. The reference electrogram may additionally have identified activation events and activation event timings associated with the activation events. Processing system 32 may identify one or more fiducial points in the characteristic signal with the same timings as the identified activation events in the reference electrogram. In other examples, processing system 32 may identify one or more particular features of the characteristic signal as fiducial points, such as the first data point of the characteristic signal. In examples where processing system 32 determines multiple fiducial points in the characteristic signal, processing system 32 may determine set data points as fiducial points, for example, every $10^{th}$, $50^{th}$, $100^{th}$, or the like data points may be fiducial points. Processing system 32 additionally determines the timings of the fiducial points within the characteristic signal.

In any event, processing system 32 may determine an activation time from the timings of the activation events and the fiducial points. For example, processing system 32 may determine a difference in timings between a fiducial point and an activation event, with the difference being the activation time for the characteristic signal. In other examples, processing system may determine multiple differences in times between fiducial points and activation times, with the average of the differences being the activation time for the characteristic signal. Processing system 32 may store such a determined activation time in memory.

Figure 9:
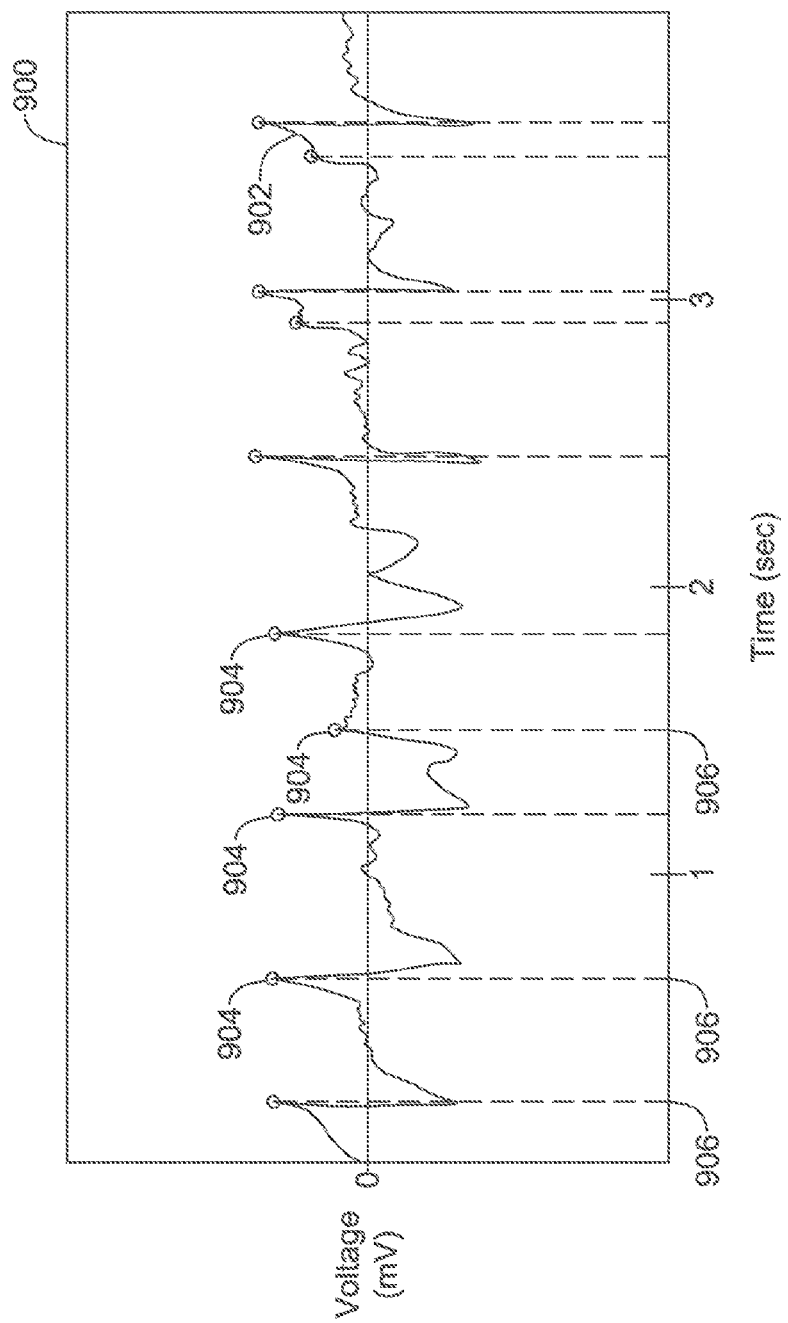
FIG. 9 is an illustration of identified peaks in a cardiac electrical signal.

As described above, processing system 32 may determine activation times for the other electrograms in the first group differently than for the characteristic signal. For example, none of the other electrograms have associated activation events and timings of activation events. Processing system 32 may begin by determining one or more activation events in the other electrograms. One technique processing system 32 may employ is to use a peak-finding algorithm to identify activation events in the other electrograms. FIG. 9 depicts graph 900 showing electrogram 902. After employing the peak finding-algorithm, processing system 32 may identify peaks 904. Each peak 904 may have an associated peak timing 906. In some examples, the peak-finding algorithm may identify peaks that do not represent activation events.

In order to reduce the number of identified peaks to peaks that only represent activation events, processing system 32 may compare the timings of the activation events in the characteristic signal to the timings of the peaks in the other electrograms. As described above, at the beginning of a physiological event, an electrical wave may propagate through the tissue adjacent to the electrodes. As this wave propagates through the tissue, each electrode may sense this wave, albeit at slightly different times. Accordingly, each electrodes may sense an activation event, but with slight differences in timing. Since activation events are already associated with the characteristic signal, the peaks in the other electrograms which identify activation events occur relatively closely in time to the timings of the activation events in the characteristic signal. Accordingly, processing system 32 may remove peaks identified in the other electrograms that fall outside of a time window defined around the timing of each activation event in the characteristic signal.

Figure 10:
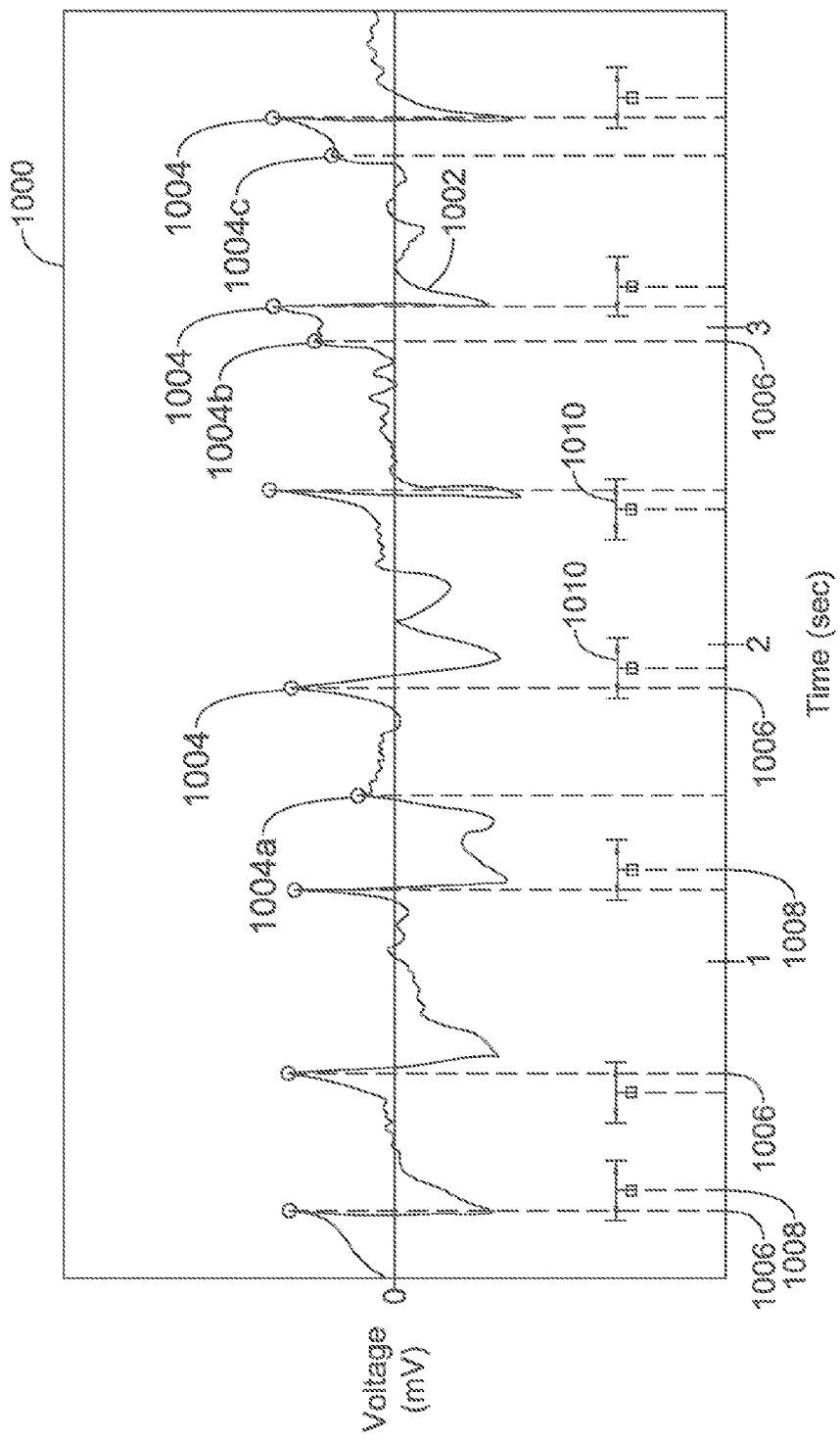
FIG. 10 is another illustration of identified peaks in a cardiac electrical signal.

FIG. 10 depicts graph 1000 which includes electrogram 1002. Electrogram 1002 is the same as electrogram 902 depicted in FIG. 9. Graph 1000 also depicts peaks 1004 that processing system identified with a peak-finding algorithm. Associated peak timings 1006 represent the times at which peaks 1004 occur. FIG. 10 also depicts activation event timings 1008. Activation event timings 1008 represent the times at which the activation events occur in the characteristic signal. Activation windows 1010 are windows of time centered around each of activation event timings 1008. Processing system may remove identified peaks whose associated peak timing does not fall within any activation window 1010, as it is unlikely that these identified peaks do not represent actual activation events. For example, processing system 32 may remove peaks 1004a, 1004b, and 1004c, as their associated peak timings 1006 do not within any activation windows 1010. Although FIGS. 9 and 10 generally depict a single electrogram, processing system 32 may perform a similar process on each other the other electrograms (e.g. each of the electrograms other than the characteristic signal) in the first group. Peak timings 1006 of remaining peaks 1004 may represent activation event timings in each of the other electrograms.

In some examples, multiple identified peaks may fall within an activation window 1010 (not shown in FIG. 10). In such examples, processing system 32 may use one or more algorithms to remove the one or more extra peaks that fall within an activation window 1010. For example, processing system 32 may employ a nearest-neighbor algorithm to find the identified peak that is closest in time to the activation event timing 1008 of the activation window 1010. Processing system 32 may then remove all identified peaks within the activation window 1010 other than the "nearest-neighbor" identified peak. In other examples, processing system 32 may use other algorithms to remove peaks that fall within an activation window.

The above process for identifying activation events in the other electrograms is just one example. In other examples, processing system 32 may use other techniques for identifying activation events in the other electrograms. For example, processing system 32 may determine a derivative of the characteristic signal and identify locations within the derivative of the characteristic signal that are less than a predetermined threshold as activation events. Processing system 32 may additionally use other techniques for determining activation events in the other electrograms.

After removing peaks in the other electrograms, or otherwise determining activation events in the other electrograms, processing system 32 may display each electrogram in the first group of electrograms at display device 40, including the determined activation events and activation event timings. In some of these examples, a user may modify the determined activation events. For example, a user may add activation events, remove determined activation events, or move determined activation events for each of the other electrograms in the first group. Processing system 32 may then store the activation events and activation event timings for each of the electrograms in the first group in memory.

Processing system 32 may then determine activation times for each of the other electrograms. For example, processing system 32 identify one or more fiducial points in each of the other electrograms. The fiducial point or points may be the same fiducial point or points as the fiducial points in the characteristic signal. For example, the timing of the fiducial point or points in the other electrograms may be the same as the timing of the fiducial point or points in the characteristic signal. Processing system 32 may then determine a difference in times between a fiducial point and an activation event for each of the other electrograms. This difference in timing is the activation time. In other examples, processing system may determine multiple differences in times between fiducial points and activation times for each of the other electrograms, with the average of the differences being the activation time. Processing system 32 may store such determined activation times in memory.

Processing system 32 may then display each of the electrograms in the second group of electrograms at display device 40. Processing system 32 may further receive input indicating activation events and activation event timings for each of the electrograms in the second group of electrograms. For example, a user may view one of the displayed electrograms and input information indicating an activation event. In some examples, the user may select a point on the electrogram with a peripheral input device, or using touch input if display device 40 is a touch-sensitive display, where the selected point represents an activation event. Processing system 32 may then determine an associated activation event timing for each received input indicating an activation event. Processing system 32 may additionally determine activation times for each of the electrograms in the second group in a similar manner as that described with respect to the characteristic signal—e.g. using one or more fiducial points and determining a difference or differences in timings of the fiducial point or points and activation events.

In this manner, processing system 32 may determine activation times for each of the electrograms in both the first and second groups of electrograms. Processing system may further populate an activation time map with these determined activation times and display the activation map at a display device, such as display device 40. FIG. 11 depicts an example activation map 1100. Activation map 1100 takes the form of a grid that is designed to display activation times for all electrograms. As described previously, these electrograms are generated based on cardiac electrical activity sensed by electrodes 24 of multiple electrode structure 20 (and in some cases are the raw sensed cardiac electrical signals). Accordingly, the determined activation times may be associated with particular electrodes, as each electrogram is generated from data sensed by a single electrode.

Space 1102 on map 1100 represents a known data point, e.g. a known activation time. Each of the spaces filled in with a value represent known data points. As described previously, in some examples, a known data point may be generated from each electrogram in the first group of electrograms. Accordingly, each filled in space represents one of the electrograms in the first group of electrograms, which is associated with the electrode labeled with a reference number the same as the combination of the row and column of the space.

In some examples, even after receiving input from a user, processing system 32 may not be able to determine activation times for one or more of the electrograms in the second group of electrograms. For example, a user may not be able to identify any activation events in one or more of the electrograms in the second group of electrograms and thus may not input any activation events to processing system 32. One reason may be that the electrode that sensed the cardiac electrical activity was not in good electrical contact with the tissue and therefore did not sense the propagating wave. Accordingly, the electrogram based off of the sensed cardiac electrical activity may not include any features that a user may identify as activation events. In such instances, processing system 32 may populate activation map 1100 with a symbol indicating an absence of an activation time for that electrode. In the example of FIG. 11, processing system displays a "?" symbol, as in space 1104. The "?" may indicate an unknown data point. In some examples, processing system 32 is unable to determine an activation time for each electrogram in the first group. In such examples, even spaces in activation map 1100 which reference electrodes/electrograms in the first group may include the "?" symbol (or other symbol indicating an unknown data point).

In some examples, processing system 32 may modify activation map 1100 in a number of different ways for display on display device 40. For example, processing system 32 may assign a unique, differentiating color to each space in table 1100. In some examples, the specific color is assigned based on the value of the activation time in the space. The color map may help a clinician identify the propagation direction of cellular firing. Activation map 1100 may display an activation time or color for known signals and not display an activation time or color for unknown and/or missing activation time data. The use of color to differentiate activation times is just an example. It is contemplated that other means may be used to differentiate activation times. For example, texture, symbols, numbers, or the like may be used as differentiating characteristics.

In order to maximize the utility of activation map 1100, it may be desirable to populate unknown activation times. Therefore, in some embodiments it may be desirable to interpolate activation times for missing signal data and populate and/or fill in the activation time map 1100 accordingly. Processing system 32 may perform any of the techniques disclosed in "MEDICAL DEVICES FOR MAPPING CARDIAC TISSUE," a provisional patent application filed on Jan. 13, 2014, No. 61/926,737, which is hereby incorporated by reference in its entirety, for assigning values to the missing data.

Figure 12:
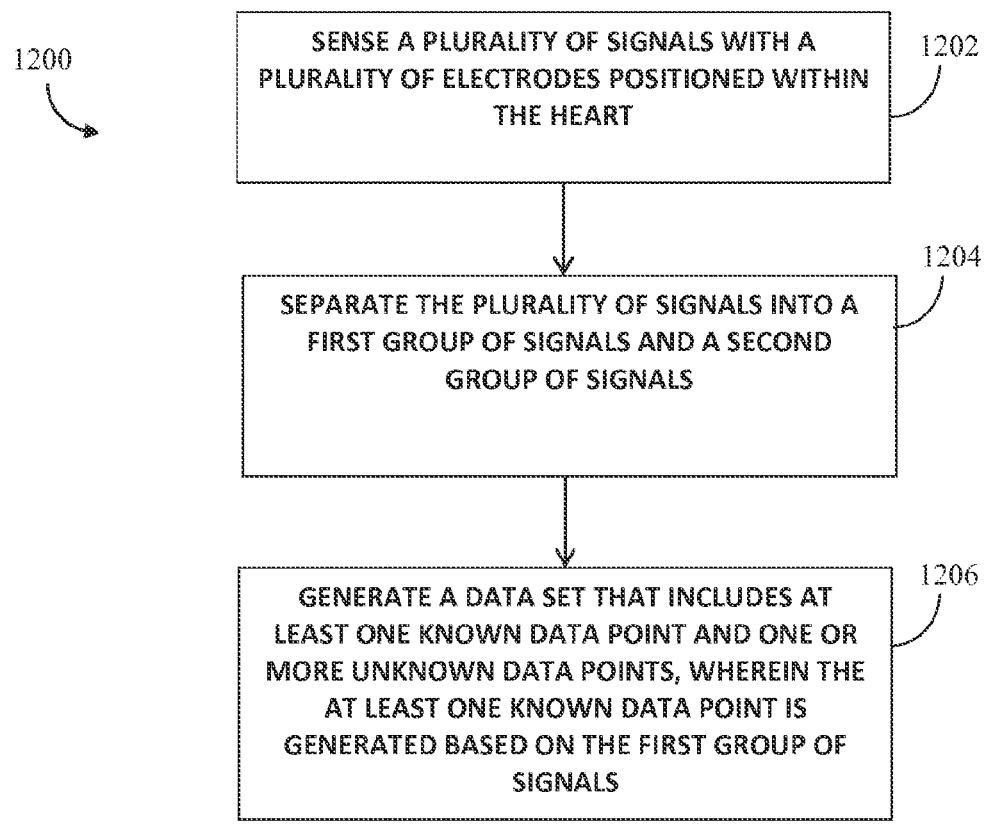
FIG. 12 is another illustrative method in accordance with this disclosure that may be performed by a catheter system, such as that depicted in FIG. 1.

FIG. 12 is a flow diagram of an illustrative method that may be implemented by a catheter system such as shown in FIG. 1. Although the method of FIG. 12 will be described with respect to the catheter system of FIG. 1, the illustrative method of FIG. 12 may be performed by any suitable catheter system.

In some examples, a catheter device, for instance catheter system 10, may include electrodes 24 which are disposed within a heart. System 10 may be configured to sense a plurality of signals with a plurality of electrodes positioned within the heart, as shown at 1202. System 10 may additionally separate the plurality of signals into a first group of signals and a second group of signals, as shown at 1204. For example, system 10 may utilize one or more signal processing, statistical, and/or clustering techniques to separate the plurality of signals in the first group of signals and the second group of signals. System 10 may additionally generate a data set that includes at least one known data point and one or more unknown data points, wherein the at least one known data point is generated based on the first group of signals, as shown at 1206. In some examples, the data points may be activation times.

Figure 13:
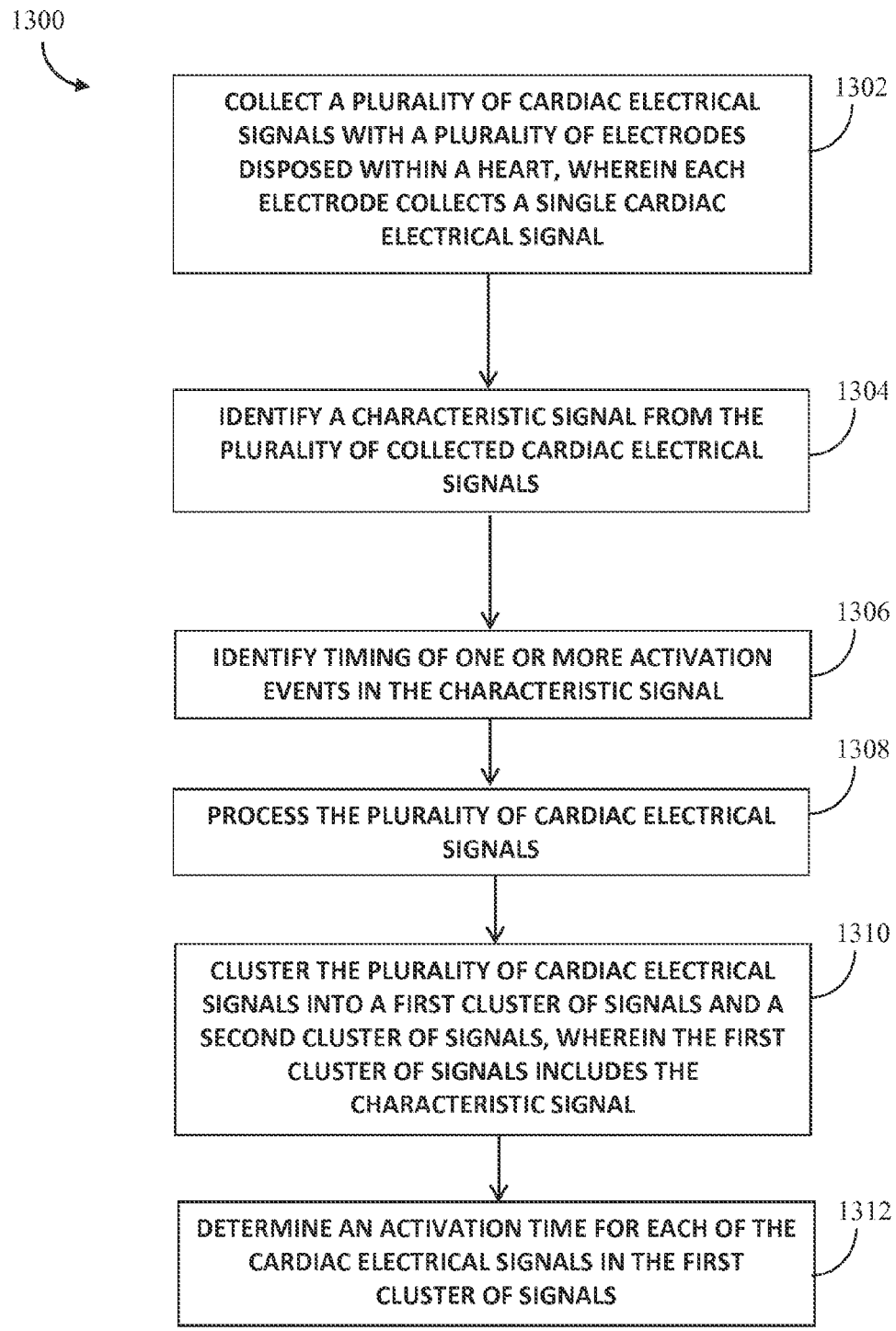
FIG. 13 is another illustrative method in accordance with this disclosure that may be performed by a catheter system, such as that depicted in FIG. 1.

FIG. 13 is a flow diagram of an illustrative method that may be implemented by a catheter system such as shown in FIG. 1. Although the method of FIG. 13 will be described with respect to the catheter system of FIG. 1, the illustrative method of FIG. 13 may be performed by any suitable catheter system.

In some examples, a catheter device, for instance catheter system 10, may include electrodes 24 which are disposed within a heart. System 10 may be configured to collect a plurality of cardiac electrical signals with a plurality of electrodes disposed within a heart, wherein each electrode collects a single cardiac electrical signal, as shown at 1302. System 10 may further be configured to identify a characteristic signal from the plurality of collected cardiac electrical signals, as shown at 1304. In some examples, system 10 may automatically identify a characteristic signal. In other examples, system 10 may receive input identifying a characteristic signal. System 10 may then identify timing of one or more activation events in the characteristic signal, as shown at 1306. Again, in some examples system 10 may determine the one or more activation events automatically. In other examples, system 10 may receive input indicating the one or more activation events.

System 10 may further process the plurality of cardiac electrical signals, as shown at 1308. For example, system 10 may perform one or more signal processing techniques on the plurality of cardiac electrical signals. Some example signal processing techniques include wavelet transforms, rectification, and filtering. System 10 may then cluster the plurality of cardiac electrical signals into a first cluster of signals and a second cluster of signals, wherein the first cluster of signals includes the characteristic signal, as shown at 1310. For example, system 10 may utilize one or more clustering techniques, such as density-based clustering techniques and/or distribution-based clustering techniques. Ultimately, system 10 may determine an activation time for each of the cardiac electrical signals in the first cluster of signals, as shown at 1312.

What is claimed is:

1. A method of identifying activation times in a plurality of signals, the method comprising:
    collecting a plurality of cardiac electrical signals with a plurality of electrodes disposed within a heart, wherein each electrode collects a single cardiac electrical signal;
    identifying a characteristic signal from the plurality of collected cardiac electrical signals;
    identifying timing of one or more activation events in the characteristic signal;
    processing the plurality of cardiac electrical signals;
    clustering the plurality of cardiac electrical signals into a first cluster of signals and a second cluster of signals, wherein the first cluster of signals includes the characteristic signal; and
    determining an activation time for each of the cardiac electrical signals in the first cluster of signals.

2. The method of claim 1, wherein processing the plurality of signals comprises one or more of the following:
    performing a wavelet transform on the plurality of signals; rectifying the plurality of signals; and
    low-pass filtering the plurality of signals.

3. The method of claim 1, wherein clustering the plurality of cardiac electrical signals into a first cluster of signals and a second cluster of signals comprises:
    performing statistical analysis on the plurality of signals; and
    performing a density-based clustering of the results of the statistical analysis, wherein the results of the density-based clustering comprises the first cluster of signals and the second cluster of signals.

4. The method of claim 3, wherein: performing statistical analysis comprises performing principal component analysis; and performing the density-based clustering comprises performing a Gaussian mixture model analysis.

5. The method of claim 1, wherein determining activation times for each of the cardiac electrical signals in the first cluster of signals comprises:
- determining an activation time for the characteristic signal based on the identified timing of the one or more activation events in the characteristic signal;
- identifying one or more peaks in each of the other cardiac electrical signals in the first cluster of signals; identifying timings of each of the identified one or more peaks in each of the other cardiac electrical signals; and
- determining activation times for each of the other cardiac electrical signals based on the identified timings of the identified one or more peaks.

6. The method of claim 5, wherein determining activation times for each of the other cardiac electrical signals based on the identified one or more peaks further comprises:
- removing one or more of the identified one or more peaks in each of the other cardiac electrical signals based on the identified timings of the one or more activation events in the characteristic signal; and
- determining activation times for each of the other cardiac electrical signals based on the remaining identified one or more peaks.

7. The method of claim 1, wherein determining activation times in each of the cardiac electrical signals in the first cluster of signals comprises:
- identifying a timing of a fiducial point in each of the signals in the first cluster of signals;
- determining a difference in timing between the fiducial point and one or more of the activation events in the characteristic signal;
- identifying timings of one or more peaks in the other cardiac electrical signals in the first cluster of signals;
- determining a difference in timing between the fiducial point and one or more of the identified one or more peaks in the other cardiac electrical signals in the first cluster of signals; and
- determining activation times based on the determined differences.

* * * * *